(12) United States Patent
Fischer et al.

(10) Patent No.: US 7,884,242 B2
(45) Date of Patent: Feb. 8, 2011

(54) N-HETEROCYCLYLPHTHALDIAMIDES AS INSECTICIDES

(75) Inventors: Rüdiger Fischer, Pulheim (DE);
Christian Funke, Leichlingen (DE);
Olga Malsam, Rösrath (DE); Tetsuya Murata, Tochigi (JP); Katsuaki Wada, Tochigi (JP); Yasushi Yoneta, Saitama (JP); Katsuhiko Shibuya, Tochigi (JP);
Eiichi Shimojo, Tochigi (JP); Christian Arnold, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 243 days.

(21) Appl. No.: 11/667,926

(22) PCT Filed: Nov. 5, 2005

(86) PCT No.: PCT/EP2005/011846

§ 371 (c)(1),
(2), (4) Date: Jul. 9, 2008

(87) PCT Pub. No.: WO2006/053643

PCT Pub. Date: May 26, 2006

(65) Prior Publication Data

US 2009/0023752 A1 Jan. 22, 2009

(30) Foreign Application Priority Data

Nov. 18, 2004 (DE) .................. 10 2004 055 582

(51) Int. Cl.
*C07C 259/04* (2006.01)
(52) U.S. Cl. ..................................... 562/623
(58) Field of Classification Search .................. 562/623
See application file for complete search history.

(56) References Cited

U.S. PATENT DOCUMENTS

| | | | |
|---|---|---|---|
| 4,053,608 | A | 10/1977 | Morisawa et al. |
| 4,181,800 | A | 1/1980 | Kamiya et al. |
| 6,362,369 | B2 | 3/2002 | Tohnishi et al. |
| 6,559,341 | B2 | 5/2003 | Tohnishi et al. |
| 6,603,044 | B1 | 8/2003 | Tohnishi et al. |
| 6,864,289 | B1 | 3/2005 | Tohnishi et al. |
| 6,875,768 | B1 | 4/2005 | Machiya et al. |
| 7,151,195 | B2 | 12/2006 | Matsuzaki et al. |
| 7,161,032 | B2 | 1/2007 | Yamaguchi et al. |
| 7,256,192 | B2 | 8/2007 | Tohnishi et al. |
| 2004/0116299 | A1 | 6/2004 | Harayama et al. |
| 2007/0299085 | A1 | 12/2007 | Wada et al. |
| 2008/0045727 | A1 | 2/2008 | Blaschke et al. |
| 2009/0118375 | A1 | 5/2009 | Fischer et al. |

FOREIGN PATENT DOCUMENTS

| | | |
|---|---|---|
| EP | 1 006 107 A2 | 6/2000 |
| EP | 1 193 254 A1 | 4/2002 |
| EP | 1 241 159 A1 | 9/2002 |
| EP | 1 215 200 B1 | 3/2005 |
| EP | 0 919 542 B1 | 8/2006 |
| EP | 1 006 102 B1 | 8/2006 |
| NL | 8102874 | 1/1983 |
| WO | WO 92/13838 A1 | 8/1992 |
| WO | WO 00/39156 A1 | 7/2000 |
| WO | WO 00/61572 A1 | 10/2000 |
| WO | WO 02/48137 A2 | 6/2002 |
| WO | WO 02/070494 A1 | 9/2002 |
| WO | WO 02/094765 A2 | 11/2002 |

OTHER PUBLICATIONS

Abdul-Ghani, M., and Tipping, A.E., "The Synthesis from 2,5-Dichloro-1,1,1,6,6,6,-hexafluoro-3,4-diazahexa-2,4-diene of 4H-3,5-Bis(trifluoromethyl)-1,2,4-triazole and some 1- and 4-Substituted Derivatives," *J. Fluor. Chem.* 48:149-152, Elsevier Sequoia (1990).

Gielen, H., et al., "A novel approach to amidines from esters," *Tetrahedron Letts.* 43:419-421, Elsevier Science Ltd. (2002).

Makosza, M., and Bialecki, M., "Synthesis of (Nitroaryl)chloromethanes via Vicarious Nucleophilic Substitution of Hydrogen," *Synlett* 1991:181-182, Georg Thieme Verlag (1991).

Sekikawa, I., and Takahashi, Y., "Synthesis of Isonipecotinoyl Analogues of Aminopterin and Folic Acid," *J. Heterocyclic Chem.* 20:807-809, Journal of Heterocyclic Chemistry (1983).

Spijker, N.M., et al., "Synthesis of a Pentasaccharide and a Heptasaccharide Corresponding to an Ovarian Glycoprotein; Studies Towards Glycosylations," *Tetrahedron* 48:6297-6316, Pergamon Press Ltd. (1992).

Taylor, E.C., and LaMattina, J.L., "Pteridines.40. Some Reactions of 2-Amino-3-cyano-5-bromomethylpyrazine and 2-Amino-3-cyano-5-methylpyrazine," *J. Org. Chem.* 42:1523-1527, American Chemical Society (1977).

(Continued)

*Primary Examiner*—James O Wilson
*Assistant Examiner*—Douglas M Willis
(74) *Attorney, Agent, or Firm*—Sterne, Kessler, Goldstein & Fox P.L.L.C.

(57) ABSTRACT

New N-heterocyclylphthaldiamides of structure (I)

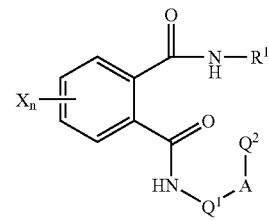

in which
n, A, $Q^1$, $Q^2$, $R^1$ and X have the meanings given in the description,
several methods for the preparation of these substances and their use for the control of pests, as well as new intermediates and methods for their preparation.

12 Claims, No Drawings

OTHER PUBLICATIONS

Taylor, E.C., et al., Pteridines. 44. A Convenient Synthesis of 6-Formylpterin[1,2], *J. Org. Chem.* 43:736-737, American Chemical Society (1978).

Werbel, L.M., et al., "Folate Antagonists. 11. Synthesis and Antimalarial Effects of 6-[(Aryloxy- and arylthio-)methyl]-2,4-pteridinediamines and—pteridinediamine 8-Oxides[1-3]," *J. Med. Chem.* 21:337-339, American Chemical Society (1978).

310 ethiprole Insecticide and 311 ethofumesate Herbicide, The Pesticide Manual 13:382, The British Library (2003).

International Search Report for International Application No. PCT/EP2005/011846, European Patent Office, Netherlands, mailed on Mar. 6, 2006.

Esp@cenet Database, English language abstract for NL 8102874 and translated claims, 3 pages (listed as document FP1 on accompanying form PTO/SB/08A), Jan. 17, 1983.

Co-pending Application, U.S. Appl. No. 12/654,384 inventors Fischer, R., et al., filed Dec. 17, 2009.

N-HETEROCYCLYLPHTHALDIAMIDES AS INSECTICIDES

This application is a National Stage of International Application No. PCT/EP2005/011846, filed Nov. 5, 2005, which claims the benefit of German Patent Application No. 10 2004 055 582.6, filed Nov. 11, 2004. The entirety of each of these applications is incorporated by reference herein.

The present application of an invention concerns novel N-heterocyclylphthaldiamides, methods for their preparation and their use as plant treatment agents and pest control agents, especially as insecticides.

It is already known that certain N-aryl phthaldiamides demonstrate insecticidal properties. (cf. U.S. Pat. Nos. 6,362,369, 6,603,044, WO 01/02354, WO 01/21576, WO 01/46124, WO 02/48137, WO 02/94765, WO 04/018415).

Since ecological and economic demands on modern plant treatment agents are continually increasing, particularly in respect to the amount applied, residue formation, selectivity, toxicity and favourable production methodology, and also because, for example, resistance problems can occur, there is the on-going task to develop new plant treatment agents that at least in certain areas are able to demonstrate advantages over known agents.

Novel N-heterocyclylphthaldiamides of structure (I) have now been found in which

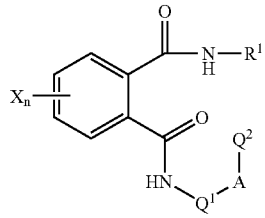

(I)

n stands for the numbers 0, 1, 2, 3 or 4,

A stands for O (oxygen), S (sulphur), SO or $SO_2$, NH or N(alkyl), or for straight chain or branched alkanediyl (alkylene), optionally substituted and optionally interrupted by O (oxygen), S (sulphur), SO or $SO_2$, NH or N(alkyl), $Q^1$ stands for an optionally substituted heterocyclic group, $Q^2$ stands for an optionally substituted heterocyclic group, $R^1$ stands for hydrogen, cyano or the group $A^1$-$X^1$, whereby $A^1$ stands for a single bond, for O (oxygen), S (sulphur), SO, $SO_2$, NH, CO, COO, or straight-chain or branched alkanediyl (alkylene) and $X^1$ stands in each case for optionally substituted alkyl, alkenyl, alkynyl, cycloalkyl, cycloalkenyl, aryl or heterocyclyl, and X stands for nitro, cyano, halogen or the group $A^2$-$X^2$, whereby $A^2$ stands for a single bond, for O (oxygen), S (sulphur), SO, $SO_2$, $OSO_2$, $NHSO_2$, CO, OCO, NHCO or alkanediyl (alkylene) and $X^2$ stands in each case for optionally substituted alkyl, alkenyl, alkynyl, cycloalkyl or aryl.

The compounds of structure (I) can also exist in the form of addition compounds with acidic or basic materials and optionally also as adducts with oxygen in the form of N-oxides.

Depending upon the nature of the substituents the compounds of structure (I) can also exist as stereoisomers, that is as geometric and/or optical isomers or as isomer mixtures of differing composition. Both the pure stereoisomers and any arbitrary mixture of these isomers are subject matter of this invention, even if here in general the discussion is limited to compounds of structure (I).

Residues substituted by halogen, for example haloalkyl, are halogenated singly or several times up to the maximum number of substituents possible. In the case of multiple halogenation the halogen atoms can be the same or different. Here halogen stands for fluorine, chlorine, bromine or iodine, especially for fluorine, chlorine or bromine.

It has been further found that N-heterocyclylphthaldiamides of structure (I) are obtained if 3-imino-2-benzofuran-1(3H)-ones of structure (II),

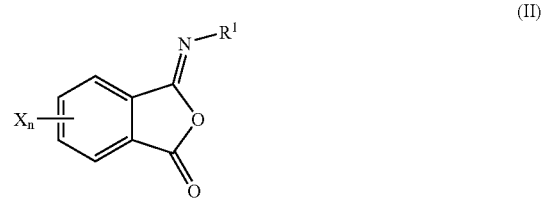

(II)

in which n, $R^1$ and X have the above meaning, are reacted substituted with heterocyclylamines of structure (III),

(III)

in which A, $Q^1$ and $Q^2$ have the above meaning, optionally in the presence of a reaction auxiliary and optionally in the presence of a diluent, and optionally the compounds of structure (I) thus obtained, commensurate with the substituent definitions, are converted into another compound of structure (I) by normal methods.

Finally it was found that the compounds of structure (I) of the invention demonstrate very interesting biological properties and are suitable for the control of zoopests such as arthropods and nematodes, especially insects, in plant protection, material protection and stock protection, as well as in the areas of household/hygiene and animal health.

The N-heterocyclylphthaldiamides of the invention are defined by the general structure (I). Preferred residue definitions of the structures given above and below are defined in the following. These definitions apply equally to both the final products of structure (I) and all intermediates.

n stands preferably for the numbers 1, 2 or 3.

n stands more preferably for the numbers 1 or 2.

A stands preferably for O (oxygen), S (sulphur), SO or $SO_2$, NH or N($C_1$-$C_4$-alkyl), or for straight-chain or branched alkanediyl (alkylene) with 1 to 10 carbon atoms, optionally substituted by cyano, halogen or $C_1$-$C_6$-alkoxy and optionally interrupted by O (oxygen), S (sulphur), SO or $SO_2$, NH or N($C_1$-$C_4$-alkyl).

A stands more preferably for straight-chain or branched alkanediyl (alkylene) with 1 to 6 carbon atoms, optionally substituted by cyano, fluorine, chlorine, bromine, methoxy, ethoxy, n- or i-propoxy, n-, i-, s- or t-butoxy and optionally interrupted by O (oxygen), S (sulphur), SO, $SO_2$, NH or N($CH_3$).

A stands most preferably for methylene, ethane-1,1-diyl(ethylidene), 2,2,2-trifluoroethane-1,1-diyl, ethane-1,2-diyl (dimethylene), propane-1,1-diyl(propylidene), propane-1,2-diyl or propane-1,3-diyl(trimethylene).

$Q^1$ stands preferably for an optionally substituted heterocyclic group with up to 10 carbon atoms and at least one heteroatom from the series O (oxygen), S (sulphur), N (nitrogen) and/or a SO or $SO_2$ group, whereby the preferred possible substituents are selected from the listing given below under X.

$Q^1$ stands more preferably for an optionally substituted monocyclic heterocyclic group of up to 5 carbon atoms and 1 to 4 N atoms and/or an O atom and/or a S atom and/or a SO or $SO_2$ group as part of the heterocycle, whereby the preferred possible substituents are selected from the listing given below under X.

$Q^1$ stands most preferably for an optionally substituted pyridine group, pyrimidine group, pyrazine group, pyridazine group, triazole group, oxadiazole group, thiadiazole group, pyrazole group, imidazole group, pyrrole group, oxazole group, isoxazole group, thiazole group, isothiazole group, furan group or thiophene group, whereby the preferred possible substituents are selected from the listing given below under X.

$Q^2$ stands preferably for an optionally substituted heterocyclic group with up to 10 carbon atoms and at least one heteroatom from the series O (oxygen), S (sulphur), N (nitrogen) and/or a SO or $SO_2$ group, whereby the preferred possible substituents are selected from the listing given below under X.

$Q^2$ stands more preferably for an optionally substituted monocyclic or bicyclic heterocyclic group with up to 9 carbon atoms and 1 to 5 N atoms and/or an O atom and/or a S atom and/or a SO or $SO_2$ group as part of the heterocycle, whereby the preferred possible substituents are selected from the listing given below under X.

$Q^2$ stands most preferably for an optionally substituted pyrrole group, pyrazole group, imidazole group, triazole group, tetrazole group, oxazole group, thiazole group, furan group or thiophene group, whereby the preferred possible substituents are selected from the listing given below under X.

$R^1$ stands preferably for hydrogen or the group $A^1$-$X^1$, where stands $A^1$ for a single bond, for O (oxygen), S (sulphur), SO, $SO_2$, NH, CO or COO, or for straight-chain or branched alkanediyl (alkylene) with 1 to 10 carbon atoms, and $X^1$ stands for alkyl with 1 to 10 carbon atoms optionally substituted by hydroxy, cyano, carbamoyl, hydroxyimino, halogen, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_6$-alkylaminosulphonyl, $C_1$-$C_6$-alkylcarbonyl, $C_1$-$C_6$-alkylcarbonylamino, $C_1$-$C_6$-alkylaminocarbonyloxy, di($C_1$-$C_6$-alkyl)aminocarbonyloxy, $C_1$-$C_6$-alkoximino, $C_1$-$C_6$-alkoxycarbonyl, $C_1$-$C_6$-alkylaminocarbonyl or di($C_1$-$C_6$-alkyl)aminocarbonyl, for alkenyl or alkynyl with in each case 2 to 10 carbon in each case optionally substituted by cyano, halogen and/or $C_1$-$C_6$-alkoxycarbonyl, for cycloalkyl or cycloalkenyl with in each case 3 to 6 carbon atoms in each case optionally substituted by cyano, halogen, $C_1$-$C_6$-alkyl, $C_1$-$C_6$-alkoxy and/or $C_1$-$C_6$-alkoxycarbonyl, for aryl with 6 or 10 carbon atoms optionally substituted by nitro, cyano, carboxy, carbamoyl, thiocarbamoyl, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-haloalkylsulphonyl, di($C_1$-$C_6$-alkyl)aminosulphonyl, $C_1$-$C_6$-alkylcarbonyl, $C_1$-$C_6$-alkoxyimino-$C_1$-$C_6$-alkyl, $C_1$-$C_6$-alkoxycarbonyl, $C_1$-$C_6$-alkylaminocarbonyl and/or di($C_1$-$C_6$-alkyl)aminocarbonyl, or for heterocyclyl with up to 10 carbon atoms, up to 5 N atoms and/or an O atom, S atom or N atom, and/or a SO group or a $SO_2$ group optionally substituted by nitro, cyano, carboxy, carbamoyl, thiocarbamoyl, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphonyl, $C_1$-$C_6$-alkylsulphonyl, $C_1$-$C_6$-haloalkylsulphonyl, di($C_1$-$C_6$-alkyl)aminosulphonyl, $C_1$-$C_6$-alkylcarbonyl, $C_1$-$C_6$-alkoxycarbonyl, $C_1$-$C_6$-alkylaminocarbonyl and/or di($C_1$-$C_6$-alkyl)aminocarbonyl.

$R^1$ stands more preferably for hydrogen or the group $A^1$-$X^1$, where $A^1$ stands for a single bond, for O (oxygen), S (sulphur), SO, $SO_2$, NH, CO or COO, or for straight-chain or branched alkanediyl (alkylene) with 1 to 6 carbon atoms, and $X^1$ stands for alkyl with 1 to 6 carbon atoms optionally substituted by hydroxy, cyano, carbamoyl, hydroxyimino, halogen, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-alkylaminosulphonyl, $C_1$-$C_5$-alkylcarbonyl, $C_1$-$C_5$-alkylcarbonylamino, $C_1$-$C_5$-alkylaminocarbonyloxy, di($C_1$-$C_5$-alkyl)aminocarbonyloxy, $C_1$-$C_5$-alkoximino, $C_1$-$C_5$-alkoxycarbonyl, $C_1$-$C_5$-alkylaminocarbonyl or di($C_1$-$C_5$-alkyl)aminocarbonyl, for alkenyl or alkynyl with in each case 2 to 6 carbon atoms in each case optionally substituted cyano, halogen and/or $C_1$-$C_5$-alkoxycarbonyl, for cycloalkyl with 3 to 6 carbon atoms or cycloalkenyl with 5 or 6 carbon atoms in each case optionally substituted by cyano, halogen, $C_1$-$C_5$-alkyl, $C_1$-$C_5$-alkoxy and/or $C_1$-$C_5$-alkoxycarbonyl, for aryl with 6 or 10 carbon atoms optionally substituted by nitro, cyano, carboxy, carbamoyl, thiocarbamoyl, halogen, $C_1$-$C_5$-alkyl, $C_1$-$C_5$-haloalkyl, $C_1$-$C_5$-alkoxy, $C_1$-$C_5$-haloalkoxy, $C_1$-$C_5$-alkylthio, $C_1$-$C_5$-haloalkylthio, $C_1$-$C_5$-alkylsulphinyl, $C_1$-$C_5$-haloalkylsulphinyl, $C_1$-$C_5$-alkylsulphonyl, $C_1$-$C_5$-haloalkylsulphonyl, di($C_1$-$C_5$-alkyl)aminosulphonyl, $C_1$-$C_5$-alkylcarbonyl, $C_1$-$C_5$-alkoxyimino-$C_1$-$C_5$-alkyl, $C_1$-$C_5$-alkoxycarbonyl, $C_1$-$C_5$-alkylaminocarbonyl and/or di($C_1$-$C_5$-alkyl)aminocarbonyl, or for heterocyclyl with up to 6 carbon atoms and up to 4 N atoms and/or a O atom, S atom and/or N atom and/or a SO group or a $SO_2$ group optionally substituted by nitro, cyano, carboxy, carbamoyl, thiocarbamoyl, halogen, $C_1$-$C_5$-alkyl, $C_1$-$C_5$-haloalkyl, $C_1$-$C_5$-alkoxy, $C_1$-$C_5$-haloalkoxy, $C_1$-$C_5$-alkylthio, $C_1$-$C_5$-haloalkylthio, $C_1$-$C_5$-alkylsulphinyl, $C_1$-$C_5$-haloalkylsulphinyl, $C_1$-$C_5$-alkylsulphonyl, $C_1$-$C_5$-haloalkylsulphonyl, di($C_1$-$C_5$-alkyl)aminosulphonyl, $C_1$-$C_5$-alkylcarbonyl, $C_1$-$C_5$-alkoxycarbonyl, $C_1$-$C_5$-alkylaminocarbonyl and/or di($C_1$-$C_5$-alkyl)aminocarbonyl.

$R^1$ stands most preferably for hydrogen or the group $A^1$-$X^1$, whereby $A^1$ stands for a single bond, for O (oxygen), S (sulphur), SO, $SO_2$, NH, CO or COO, or for methylene, ethane-1,1-diyl (ethylidene), ethane-1,2-diyl(dimethylene), propane-1,1-diyl(propylidene), propane-1,2-diyl or propane-1,3-diyl(trimethylene), and $X^1$ stands for methyl, ethyl, n- or i-propyl, n-, i-, s- or t-butyl, n-, i-, s-, t- or neo-pentyl in each case optionally substituted by hydroxy, cyano, carbamoyl, hydroximino, fluorine, chlorine, bromine or iodine, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, propylsulphinyl, methylsulphonyl, ethylsulphonyl, methylaminosulphonyl, ethylaminosulphonyl, n- or i-propylaminosulphonyl, n-, i-, s- or t-butylaminosulphonyl, acetyl, propionyl, n- or i-butyroyl, acetylamino, propionylamino, n- or i-butyroylamino, methylaminocarbonyloxy, ethylaminocarbonyloxy, n- or i-propylaminocarbonyloxy, dimethylaminocarbonyloxy, diethylaminocarbonyloxy, methoximino, ethoximino, propoximino, butoximino, methoxycarbonyl, ethoxycarbonyl, n- or i-propoxycarbonyl, n-, i-, s- or t-butoxycarbonyl, methylaminocarbonyl, ethylaminocarbonyl, n- or i-propylaminocarbonyl, dimethylaminocarbonyl or diethylaminocarbonyl, for ethenyl, propenyl, butenyl, pentenyl, ethynyl, propynyl, butynyl or pentinyl in each case optionally substituted by cyano, fluorine, chlorine, bromine, methoxycarbonyl, ethoxycarbonyl, n- or i-propoxycarbonyl, n-, i-, s- or t-butoxycarbonyl, for cyclopropyl, cyclobutyl, cyclopentyl, cyclohexyl, cyclopentenyl or cyclohexenyl in each case optionally substituted by cyano, fluorine, chlorine, bromine, methyl, ethyl, n- or i-propyl, methoxy, ethoxy, n- or i-propoxy, methoxycarbonyl, ethoxycarbonyl n- or i-propoxycarbonyl, for phenyl optionally substituted by nitro, cyano, carboxy, carbamoyl, thiocarbamoyl, fluorine, chlorine, bromine, iodine, methyl, ethyl, n- or i-propyl, n-, i-, s- or t-butyl, fluoromethyl, chloromethyl, difluoromethyl, dichloromethyl, trifluoromethyl, trichlormethyl, fluoroethyl, chloroethyl, difluoroethyl, dichloroethyl, trifluoroethyl, trichloroethyl, chlorofluoroethyl, chlorodifluoroethyl, fluorodichloroethyl, tetrafluoroethyl, pentafluoroethyl, methoxy, ethoxy, n- or i-propoxy, n-, i-, s- or t-butoxy, fluoromethoxy, difluoromethoxy, trifluoromethoxy, chlorodifluoromethoxy, fluoroethoxy, chloroethoxy, difluoroethoxy, dichloroethoxy, chlorofluoroethoxy, chlorodifluoroethoxy, trifluoroethoxy, tetrafluoroethoxy, pentafluoroethoxy, methylthio, ethylthio, n- or i-propylthio, n-, i-, s- or t-butylthio, difluoromethylthio, trifluoromethylthio, chlorodifluoromethylthio, methylsulphinyl, ethylsulphinyl, propylsulphinyl, trifluoromethylsulphinyl, methylsulphonyl, ethylsulphonyl, trifluoromethylsulphonyl, dimethylaminosulphonyl, acetyl, propionyl, n- or i-butyroyl, methoximinomethyl, ethoxyiminomethyl, n- or i-propoximinomethyl, methoximinoethyl, ethoximinoethyl, methoximinopropyl, ethoximinopropyl, methoxycarbonyl, ethoxycarbonyl, n- or i-propoxycarbonyl, n-, i-, s- or t-butoxycarbonyl, methylaminocarbonyl, ethylaminocarbonyl, n- or i-propylaminocarbonyl, dimethylaminocarbonyl and/or diethylaminocarbonyl, or for furyl, tetrahydrofuryl, thienyl, tetrahydrothienyl or pyridyl in each case optionally substituted by nitro, cyano, carboxy, carbamoyl, thiocarbamoyl, fluorine, chlorine, bromine, iodine, methyl, ethyl, n- or i-propyl, n-, i-, s- or t-butyl, fluoromethyl, chloromethyl, difluoromethyl, dichloromethyl, trifluoromethyl, trichloromethyl, fluoroethyl, chloroethyl, difluoroethyl, dichloroethyl, trifluoroethyl, trichloroethyl, chlorofluoroethyl, chlorodifluoroethyl, fluorodichloroethyl, tetrafluoroethyl, pentafluoroethyl, methoxy, ethoxy, n- or i-propoxy, n-, i-, s- or t-butoxy, fluoromethoxy, difluoromethoxy, trifluoromethoxy, chlorodifluoromethoxy, fluoroethoxy, chloroethoxy, difluoroethoxy, dichloroethoxy, chlorofluoroethoxy, chlorodifluoroethoxy, trifluoroethoxy, tetrafluoroethoxy, pentafluoroethoxy, methylthio, ethylthio, n- or i-propylthio, n-, i-, s- or t-butylthio, difluoromethylthio, trifluoromethylthio, chlorodifluoromethylthio, methylsulphinyl, ethylsulphinyl, propylsulphinyl, trifluoromethylsulphinyl, methylsulphonyl, ethylsulphonyl, trifluoromethylsulphonyl, dimethylaminosulphonyl, acetyl, propionyl, n- or i-butyroyl, methoximinomethyl, ethoxyiminomethyl, n- or i-propoximinomethyl, methoximinoethyl, ethoximinoethyl, methoximinopropyl, ethoximinopropyl, methoxycarbonyl, ethoxycarbonyl, n- or i-propoxycarbonyl, n-, i-, s- or t-butoxycarbonyl, methylaminocarbonyl, ethylaminocarbonyl, n- or i-propylaminocarbonyl, dimethylaminocarbonyl and/or diethylaminocarbonyl.

X stands preferably for nitro, cyano, halogen or the group $A^2$-$X^2$, whereby $A^2$ stands for a single bond, for O (oxygen), S (sulphur), SO, $SO_2$, $OSO_2$, $NHSO_2$, CO, OCO or NHCO, or for straight chain or branched alkanediyl (alkylene) with 1 to 10 carbon atoms and $X^2$ stands for alkyl with 1 to 10 carbon atoms optionally substituted by hydroxy, cyano, halogen, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino or $C_1$-$C_6$-alkoxycarbonyl, for alkenyl or alkynyl with in each case 2 to 10 carbon atoms in each case optionally substituted by cyano, halogen and/or $C_1$-$C_6$-alkoxy-carbonyl, for cycloalkyl with 3 to 6 carbon atoms optionally substituted by cyano, halogen and/or $C_1$-$C_6$-alkyl, or for aryl with 6 or 10 carbon atoms optionally substituted by nitro, cyano, carboxy, carbamoyl, thiocarbamoyl, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, di($C_1$-$C_6$-alkyl)aminosulphonyl, $C_1$-$C_6$-alkylcarbonyl, $C_1$-$C_6$-alkoximino-$C_1$-$C_6$-alkyl, $C_1$-$C_6$-alkoxy-carbonyl, $C_1$-$C_6$-alkylaminocarbonyl and/or di($C_1$-$C_6$-alkyl)aminocarbonyl.

X stands more preferably for nitro, cyano, halogen or the group $A^2$-$X^2$, whereby $A^2$ stands for a single bond, for O (oxygen), S (sulphur), SO, $SO_2$, $OSO_2$, $NHSO_2$, CO, OCO or NHCO, or for straight-chain or branched alkanediyl (alkylene) with 1 to 6 carbon atoms and $X^2$ for alkyl with 1 to 6 carbon atoms optionally substituted by hydroxy, cyano, halogen, $C_1$-$C_5$-alkoxy, $C_1$-$C_5$-alkylthio, $C_1$-$C_5$-alkylsulphinyl, $C_1$-$C_5$-alkylsulphonyl, $C_1$-$C_5$-alkylcarbonyl, $C_1$-$C_5$-alkoximino or $C_1$-$C_5$-alkoxycarbonyl, for in each case alkenyl or alkynyl with in each case 2 to 6 carbon atoms optionally substituted by cyano, halogen and/or $C_1$-$C_5$-alkoxycarbonyl, for cycloalkyl with 3 to 6 carbon atoms optionally substituted by cyano, halogen and/or $C_1$-$C_5$-alkyl, or for aryl with 6 or 10 carbon atoms optionally substituted by nitro, cyano, carboxy, carbamoyl, thiocarbamoyl, halogen, $C_1$-$C_5$-alkyl, $C_1$-$C_5$-haloalkyl, $C_1$-$C_5$-alkoxy, $C_1$-$C_5$-haloalkoxy, $C_1$-$C_5$-alkyl-thio, $C_1$-$C_5$-haloalkylthio, $C_1$-$C_5$-alkylsulphinyl, $C_1$-$C_5$-haloalkylsulphinyl, $C_1$-$C_5$-alkylsulphonyl, $C_1$-$C_5$-haloalkylsulphonyl, di($C_1$-$C_5$-alkyl)aminosulphonyl, $C_1$-$C_5$-alkylcarbonyl, $C_1$-$C_5$-alkoximino-$C_1$-$C_6$-alkyl, $C_1$-$C_5$-alkoxycarbonyl, $C_1$-$C_5$-alkylaminocarbonyl and/or di($C_1$-$C_5$-alkyl)aminocarbonyl.

X stands most preferably for nitro, cyano, fluorine, chlorine, bromine, iodine or the group $A^2$-$X^2$, whereby $A^2$ stands for a single bond, for O (oxygen), S (sulphur), SO, $SO_2$, $OSO_2$, $NHSO_2$, CO, OCO or NHCO, or for methylene, ethane-1,1-diyl(ethylidene), ethane-1,2-diyl (dimethylene), propane-1,1-diyl(propylidene), propane-1,2-diyl or propane-1,3-diyl (trimethylene) and $X^2$ stands for methyl, ethyl, n- or i-propyl, n-, i-, s- or t-butyl in each case optionally substituted by hydroxy, cyano, fluorine, chlorine, bromine, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, propylsulphinyl, methylsulphonyl, ethylsulphonyl, acetyl, propionyl, n- or i-butyroyl, methoximino, ethoximino, n- or i-propoximino, methoxycarbonyl, ethoxycarbonyl, n- or i-propoxycarbonyl, n-, i-, s- or t-butoxycarbonyl, for ethenyl, propenyl, butenyl, pentenyl, ethynyl, propynyl, butynyl or pentinyl in each case optionally substituted by cyano, fluorine, chlorine, bromine, methoxycarbonyl, ethoxycarbonyl, n- or i-propoxycarbonyl, for cyclopropyl, cyclobutyl, cyclopentyl or cyclohexyl optionally substituted by cyano, fluorine, chlorine, bromine, methyl, ethyl, n- or i-propyl, or for phenyl optionally substituted by nitro, cyano, carboxy, carbamoyl, thiocarbamoyl, fluorine, chlorine, bromine, iodine, methyl, ethyl, n- or i-propyl, n-, i-, s- or t-butyl, trifluormethyl, methoxy, ethoxy, n- or i-propoxy, n-, i-, s- or t-butoxy, di-fluoromethoxy, trifluoromethoxy, methylthio, ethylthio, n- or i-propylthio, n-, i-, s- or t-butylthio, difluoromethylthio, trifluoromethylthio, methylsulphinyl, ethylsulphinyl, trifluoromethylsulphinyl, methylsulphonyl, ethylsulphonyl, trifluoromethylsulphonyl, dimethylaminosulphonyl, acetyl, propionyl, n- or i-butyroyl, methoximinomethyl, ethoximinomethyl, methoximinoethyl, ethoximinoethyl, methoxycarbonyl, ethoxycarbonyl, n- or i-propoxycarbonyl, methylaminocarbonyl, ethylaminocarbonyl, n- or i-propylaminocarbonyl and/or dimethylaminocarbonyl.

A more particularly preferred group are the compounds of structure (IA)

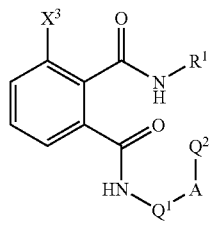

(IA)

in which

A stands for methylene, $Q^1$ stands for one of the following heterocyclic groups,

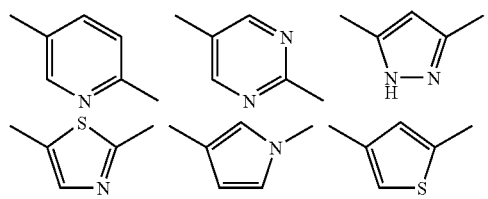

whereby these groups in each case optionally contain one or optionally two substituents from the series nitro, cyano, fluorine, chlorine, bromine, iodine, methyl, ethyl, trifluoromethyl, methoxy, ethoxy, methylthio, ethylthio, methylsulphinyl, ethylsulphinyl, methylsulphonyl, ethylsulphonyl, $Q^2$ stands for one of the following heterocyclic groups,

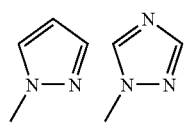

whereby these groups in each case optionally contain substituents from the series cyano, fluorine, chlorine, bromine, iodine, methyl, ethyl, n- or i-propyl, n-, i-, s- or t-butyl, fluoromethyl, difluoromethyl, trifluoromethyl, chlorodifluoromethyl, fluoroethyl, chloroethyl, difluoroethyl, dichloroethyl, chlorofluoroethyl, trifluoroethyl, trichloroethyl, chlorodifluoroethyl, fluorodichloroethyl, tetrafluoroethyl, pentafluoroethyl, hexafluoropropyl, heptafluoropropyl, methoxy, ethoxy, methylthio, ethylthio, methylsulphinyl, ethylsulphinyl, methylsulphonyl, ethylsulphonyl, $R^1$ stands for the group $A^1$-$X^1$, whereby $A^1$ stands for a single bond and $X^1$ stands for methyl, ethyl, n- or i-propyl, n-, i-, s- or t-butyl, in each case optionally substituted by hydroxy, cyano, carbamoyl, hydroximino, fluorine, chlorine, bromine or iodine, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, propylsulphinyl, methylsulphonyl, ethylsulphonyl, methylaminosulphonyl, ethylaminosulphonyl, n- or i-propylaminosulphonyl, n-, i-, s- or t-butylaminosulphonyl, acetyl, propionyl, n- or i-butyroyl, acetylamino, propionylamino, n- or i-butyroylamino, methylaminocarbonyloxy, ethylaminocarbonyloxy, n- or i-propylaminocarbonyloxy, dimethylaminocarbonyloxy, diethylaminocarbonyloxy, methoximino, ethoximino, propoximino, butoximino, methoxycarbonyl, ethoxycarbonyl, n- or i-propoxycarbonyl, n-, i-, s- or t-butoxycarbonyl, methylaminocarbonyl, ethylaminocarbonyl, n- or i-propylaminocarbonyl, dimethylaminocarbonyl or diethylaminocarbonyl, and $X^3$ stands for chlorine, bromine, iodine, methylsulphonyloxy or ethylsulphonyloxy.

A most particularly preferred group are the compounds of structure (IA)

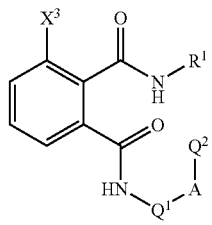

(IA)

in which

A stands for methylene, $Q^1$ stands for one of the following heterocyclic groups,

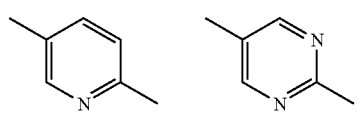

whereby these groups in each case optionally contain substituents from the series nitro, cyano, fluorine, chlorine, bromine, iodine, methyl, ethyl, trifluoromethyl, methoxy, ethoxy, methylthio, ethylthio, methylsulphinyl, ethylsulphinyl, methylsulphonyl, ethylsulphonyl—most preferably methyl.

$Q^1$ in addition stands for the following heterocyclic group,

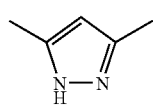

whereby this group also optionally contains substituents from the series nitro, cyano, fluorine, chlorine, bromine, iodine, methyl, ethyl, trifluoromethyl, methoxy, ethoxy, methylthio, ethylthio, methylsulphinyl, ethylsulphinyl, methylsulphonyl, ethylsulphonyl—most preferably methyl, $Q^2$ stands for one of the following heterocyclic groups,

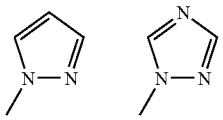

whereby these groups optionally contain substituents from the series cyano, fluorine, chlorine, bromine, iodine, methyl, ethyl, n- or i-propyl, n-, i-, s- or t-butyl, fluoromethyl, difluoromethyl, trifluoromethyl, chlorodifluoromethyl, fluoroethyl, chloroethyl, difluoroethyl, dichloroethyl, chlorofluoroethyl, trifluoroethyl, trichloroethyl, chlorodifluoroethyl, fluorodichloroethyl, tetrafluoroethyl, pentafluoroethyl, hexafluoropropyl, heptafluoropropyl, methoxy, ethoxy, methylthio, ethylthio, methylsulphinyl, ethylsulphinyl, methylsulphonyl, ethylsulphonyl—most preferably trifluoromethyl, further most preferred substituents for $Q^2$ are fluorine, iodine, difluoromethyl, pentafluoroethyl, heptafluoropropyl and methylsulphonyl, and $R^1$ stands for 1-methyl-2-methylthioethyl, 1-methyl-2-ethylthioethyl, 1-methyl-2-methylsulphinylethyl, 1-methyl-2-ethylsulphinylethyl, 1-methyl-2-methylsulphonylethyl, 1-methyl-2-ethylsulphonylethyl—most preferably for (S)-1-methyl-2-methylthioethyl, (S)-1-methyl-2-ethylthioethyl, (S)-1-methyl-2-methylsulphinylethyl, (S)-1-methyl-2-ethylsulphinylethyl, (S)-1-methyl-2-methylsulphonylethyl, (S)-1-methyl-2-ethylsulphonylethyl, and $X^3$ stands for chlorine, bromine, iodine or methylsulphonyloxy.

A most particularly preferred group are the compounds of structure (IA)

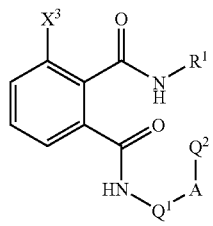
(IA)

in which

A stands for methylene, $Q^1$ stands for one of the following heterocyclic groups,

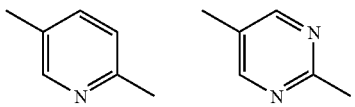

whereby these groups in each case optionally contain substituents from the series fluorine, chlorine, bromine, iodine, methyl—most preferably methyl, $Q^1$ also stands for the following heterocyclic group,

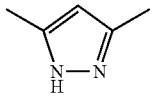

whereby this group optionally contains substituents from the series fluorine, chlorine, bromine, iodine, methyl, most particularly methyl, $Q^2$ stands for on of the following heterocyclic groups,

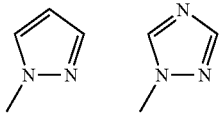

whereby these groups in each case optionally contain substituent from the series fluorine, iodine, methyl, difluoromethyl, trifluoromethyl, chlorodifluoromethyl, fluoroethyl, chloroethyl, difluoroethyl, dichloroethyl, chlorofluoroethyl, trifluoroethyl, trichloroethyl, chlorodifluoroethyl, fluorodichloroethyl, tetrafluoroethyl, pentafluoroethyl, hexafluoropropyl, heptafluoropropyl, methylsulphonyl—most preferably trifluoromethyl, further most preferred substituents for $Q^2$ are fluorine, iodine, difluoromethyl, pentafluoroethyl, heptafluoropropyl and methylsulphonyl, and $R^1$ stands for 1-methyl-2-methylthioethyl, 1-methyl-2-methylsulphinylethyl, 1-methyl-2-methylsulphonylethyl—most preferably for (S)-1-methyl-2-methylthioethyl, (S)-1-methyl-2-methylsulphinylethyl, (S)-1-methyl-2-methylsulphonylethyl, and $X^3$ stands for chlorine, bromine, iodine.

The above defined general and preferred residue definitions apply both to the final products of structure (I) and correspondingly in each case the starting materials and intermediates necessary for preparation. These residue definitions can be arbitrarily combined with each other, including between the given preferred ranges.

Preferred according to the invention are the compounds of structure (I) in which a combination of meanings given as preferred in the above is present.

More preferred according to the invention are the compounds of structure (I) in which a combination of meanings given as more preferred in the above is present.

Most preferred according to the invention are the compounds of structure (I) in which a combination of meanings given as most preferred in the above is present.

Most particularly preferred according to the invention are the compounds of structure (I) in which a combination of meanings given as most particularly preferred in the above is present.

In the residue definitions given above and the following hydrocarbon residues such as alkyl—also in combination with heteroatoms as in alkoxy—are as far as possible in each case straight-chain or branched.

Depending upon the type of substituent defined above the compounds of structure (I) can possess acidic or basic properties and can form salts. If the compounds of structure (I) bear hydroxy, carboxy or other groups inducing acidic properties these compounds may be converted into salts with bases. Suitable bases are, for example, hydroxides, carbonates, hydrogen carbonates of the alkali and alkaline earth metals, especially those of sodium, potassium, magnesium and calcium, also ammonia, primary, secondary and tertiary amines with $(C_1\text{-}C_4)$-alkyl residues as well as mono-, di- and trialkanolamines of $(C_1\text{-}C_4)$-alkanols. If the compounds of structure (I) bear amino, alkylamino or other groups inducing basic properties these compounds may be converted into salts with acids. Suitable acids are, for example, mineral acids such as hydrochloric, sulphuric and phosphoric acid, organic acids such as acetic acid or oxalic acid, and acid salts such as $NaHSO_4$ and $KHSO_4$. The salts thus obtained also exhibit fungicidal, insecticidal, acaricidal and miticidal properties.

Subject matter of the invention is also the salt-like derivatives formed from compounds of structure (I) by conversion with basic and acidic compounds as well as N-oxides prepared by normal oxidation methods.

If, for example, (3Z)-4-bromo-3-{[(1S)-2-(ethylthio)-1-methyl-ethyl]imino}-2-benzofuran-1(3H)-one and 2-methyl-6-{[5-methyl-3-(trifluoromethyl)-1H-pyrazol-1-yl]methyl}pyridine-3-amine are used as starting materials the reaction course of the method of the invention can be outlined by the following reaction scheme:

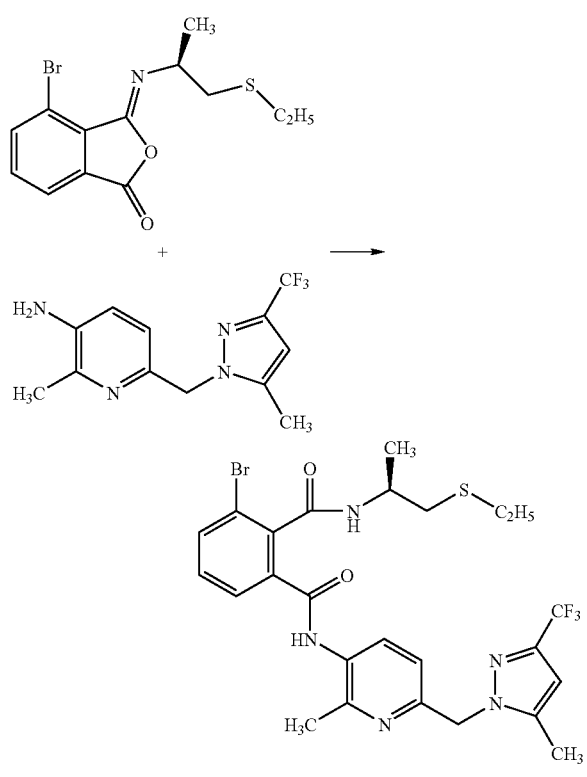

The 3-imino-2-benzofuran-1(3H)-ones used as starting materials for the preparation of compounds of structure (I) of the invention are defined in general by structure (II). In structure (II) n, $R^1$ and X have respectively preferably or especially those meanings already defined above as respectively preferred or more preferred for n, $R^1$ and X in connection with the description of the compounds of the invention of structure (I).

The starting materials of structure (II) are known and/or can be prepared by known methods (cf. EP-A 0 919 542, EP-A 1 006 102, EP-A 1 006 107, U.S. Pat. No. 6,559,341, WO 01/21576, WO 02/88075, WO 02/94765, WO 03/093228); they are in part also subject matter of a previous application (cf. European Patent Application No. 04020618.7 of 31.08.2004; cf. the preparation examples).

The substituted heterocyclylamines further used as starting materials for the preparation according to the invention of compounds of structure (I) of the invention are defined in general by structure (III) In structure (III) A, $Q^1$ and $Q^2$ have respectively preferably or especially those meanings already defined above as respectively preferred or more preferred for A, $Q^1$ and $Q^2$ in connection with the description of the compounds of the invention of structure (I).

The starting materials of structure (III) are known and/or can be prepared by known methods (cf. J. Heterocycl. Chem. 20 (1983), 807-809; J. Med. Chem. 21 (1978), 331-337; J. Org. Chem. 42 (1977), 1523-1527; loc. cit. 43 (1978), 736-737; WO 00/61572; WO 02/070494).

Hitherto unknown in the literature and as new materials subject matter of the invention are the azolylmethylazinamines of structure (IIIa)

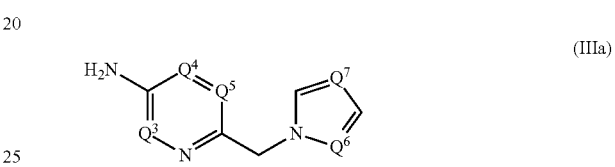

in which
$Q^3$, $Q^4$, $Q^5$, $Q^6$ and $Q^7$ stand in each case for CH or N (nitrogen), whereby in the two heterocyclic groups the H atoms in the CH positions can in each case also be substituted by one of the substituents X defined above.

The new azolylmethylazinamines of structure (IIIa) are obtained when (a) azolylmethylnitroazine of structure (IV)

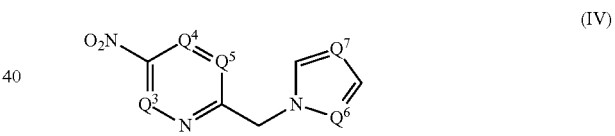

in which $Q^3$, $Q^4$, $Q^5$, $Q^6$ and $Q^7$ have the meaning defined above,
are reacted with normal reducing agents, for example with tin(II) chloride/hydrochloric acid, optionally in the presence of diluents, for example ethanol, at temperatures between 0° C. and 100° C. (cf. the preparation examples), or—for the case, that $Q^3$ and $Q^4$ stand for CH and $Q^5$ stands for N—

(b) azolylmethylpyrimidine carboxylate esters of structure (V)

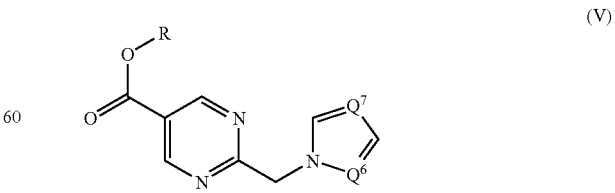

in which $Q^3$, $Q^4$, $Q^5$, $Q^6$ and $Q^7$ have the meaning defined above and
R stands for alkyl, especially methyl or ethyl, are hydrolysed in the normal way, for example by reaction with potassium hydroxide in aqueous ethanol at temperature between 0° C. and 100° C., the corresponding carboxylic acids are reacted with diphenyl phosphoryl azide in the presence of a nitrogen base, for example triethylamine, and in the presence of an alcohol, for example t-butanol, at temperatures between 0° C. and 150° C., and the N-azolylmethylpyrimidinyl carbamates of structure (VI) thus obtained

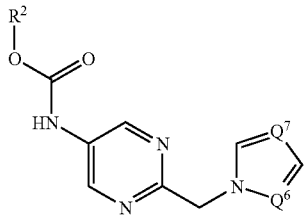

(VI)

in which
$Q^6$ and $Q^7$ have the meaning defined above and
$R^2$ stands for alkyl, preferably for $C_1$-$C_4$-alkyl, especially t-butyl,
are cleaved by reaction with a strong acid, for example trifluoroacetic acid, optionally in the presence of a diluent, for example methylene chloride, at temperatures between −10° C. and +50° C. (cf. preparation examples).

The azolylmethylnitroazines of structure (IV) required for synthesis variant (a) are hitherto unknown in the literature. The new azolylmethylnitroazines of structure (IV) are obtained when halomethylnitroazines of structure (VII)

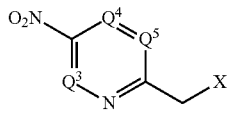

(VII)

in which
$Q^3$, $Q^4$ and $Q^5$ have the meaning defined above and
$X^4$ stands for halogen, especially for chlorine or bromine,
are reacted with azoles of structure (VIII)

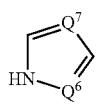

(VIII)

in which $Q^6$ and $Q^7$ have the meaning defined above,
optionally in the presence of a basic reaction auxiliary such as potassium carbonate and optionally in the presence of diluent such as N,N-dimethylformamide at temperatures between 0° C. and 150° C. (cf. preparation examples).

The precursors of structures (VI) and (VIII) are known and/or can be prepared by known methods (cf. Synlett 3 (1991), 181-182; U.S. Pat. No. 4,053,608; preparation examples).

The azolylmethylpyrimidine carboxylate esters of structure (V) required for synthesis variant (b) and the corresponding carboxylic acids are hitherto unknown in the literature and as new materials are also subject matter of the present application The intermediate N-azolylmethylpyrimidinyl carbamates of structure (VI) are also hitherto unknown in the literature. The N-azolylmethylpyrimidinyl carbamates of structure (VI) are as new materials also subject matter of the present application.

The new azolylmethylpyrimidine carboxylate esters of structure (V) are obtained when azolylacetamidines of the structure (IX),

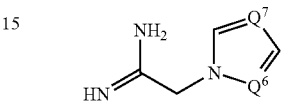

(IX)

in which $Q^6$ and $Q^7$ have the meaning defined above,
—or their acid adducts, for example the hydrochlorides— are reacted with suitable 2-alkoxymethylene-3-oxo-alkane carboxylate esters in the presence of a basic reaction auxiliary, for example sodium ethylate, and in the presence of a diluent, for example ethanol, at temperatures between −10° C. and +120° C. (cf. the preparation examples).

Azolylacetamidines of structure (IX) are known or can be prepared by known methods. Thus azoles of the structure (VIII) can be reacted for example with ethyl bromoacetate to an azolyl acetate (Abdul-Ghani et al., Journal of Fluorine Chemistry 1990, 48(1), 149-52), which can then be reacted further to the amidine of structure (IX) (Gielen et al., Tetrahedron Lett. 2002, 43, 419-422).

Also hitherto unknown in the literature and as new materials subject matter of the present application are the azolylmethyl compounds of structure (IIIb),

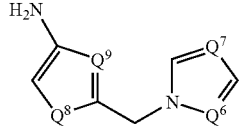

(IIIb)

in which
$Q^6$ and $Q^7$ have the meaning defined above,
$Q^8$ stands for O (oxygen) or S (sulphur) and
$Q^9$ stands for N (nitrogen) or CH whereby, however, the H atoms in the CH positions of the heterocyclic groups can in each case also be replaced by one of the above defined substituents X.

The new azolylmethyl compounds of structure (IIIb) are obtained when the corresponding nitro compounds of structure (X),

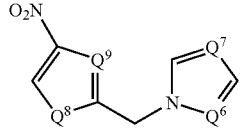

(X)

in which $Q^6$, $Q^7$, $Q^8$ and $Q^9$ have the meaning defined above, are reacted with normal reducing agents such as tin(II) chloride/hydrochloric acid, optionally in the presence of a diluent, for example ethanol, at temperatures between 0° C. and 100° C. (cf. the preparation examples).

The nitro compounds of structure (X) are hitherto unknown in the literature. They can be prepared by known methods from the corresponding precursors of structure (XI),

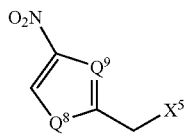
(XI)

in which $Q^8$ and $Q^9$ have the meaning defined above and $X^5$ stands for halogen, especially chlorine or bromine, or for alkylsulphonyloxy, especially methylsulphonyloxy or ethylsulphonyloxy, and azolene of the structure (VIII)

(VIII)

in which $Q^6$ and $Q^7$ have the meaning defined above, optionally in the presence of a basic reaction auxiliary, for example potassium carbonate, and optionally in the presence of a diluent, for example acetonitrile, at temperatures between 0° C. and 120° C. (cf. the preparation examples).

The nitro compounds of structure (XI) are known or can be prepared by known methods. Thus, for example, the corresponding carboxylic acids or aldehydes are first reduced to the alcohol ($X^5$=hydroxy) and then reacted with a sulphonyl chloride to the corresponding sulphonate (see synthesis example X-1). In addition the alcohols can be brominated by known methods.

In addition hitherto unknown in the literature and as new materials subject matter of the present application are the azolylmethyl compounds of structure (IIIc),

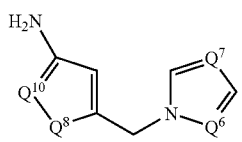
(IIIc)

in which $Q^6$, $Q^7$ and $Q^8$ have the meaning defined above, $Q^{10}$ stands for N (nitrogen) or CH whereby, however, the H atoms in the CH positions of the heterocyclic groups can in each case also be replaced by one of the above defined substituents X.

The new azolylmethyl compounds of structure (IIIb) are obtained when the corresponding nitro compounds of structure (XII),

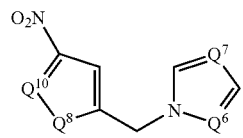
(XII)

in which $Q^6$, $Q^7$, $Q^8$ and $Q^{10}$ have the meaning defined above, are reacted with normal reducing agents, for example tin(II) chloride/hydrochloric acid, optionally in the presence of, for example, ethanol at temperatures between 0° C. and 100° C. (cf. the preparation examples).

The nitro compounds of structure (XII) are hitherto unknown in the literature. They can be prepared by known methods from the corresponding precursors of structure (XIII),

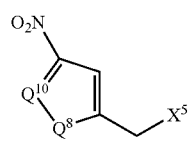
(XIII)

in which $Q^8$ and $Q^{10}$ have the meaning defined above, and $X^5$ stands for halogen, especially chlorine or bromine, or for alkylsulphonyloxy, especially methylsulphonyloxy or ethylsulphonyloxy, and azoles of structure (VIII),

(VIII)

in which $Q^6$ and $Q^7$ have the meaning defined above, optionally in the presence of a basic reaction auxiliary, for example potassium carbonate, and optionally in the presence of a diluent, for example acetonitrile, at temperatures between 0° C. and 120° C. (cf. the preparation examples).

The nitro compounds of structure (XIII) are known or can be prepared by known methods. Thus, for example, analogous to the preparation of the nitro compounds of structure (XI) the corresponding carboxylic acids (or their esters) or aldehydes are first reduced to the alcohol ($X^5$=hydroxy) and then reacted with a sulphonyl chloride to the corresponding sulphonates. In addition the alcohols can be brominated by known methods.

The method of the invention for the preparation of the novel compounds of structure (I) is advantageously carried out in the presence of a reaction auxiliary. Suitable reaction auxiliaries are particularly protic acids and Lewis acids, especially protic acids. These include, for example, hydrogen chloride or hydrochloric acid, hydrogen bromide, sulphuric acid, phosphoric acid, acetic acid, trifluoroacetic acid, methane sulphonic acid, benzene sulphonic acid and p-toluene sulphonic acid.

The method of the invention for the preparation of the novel compounds of structure (I) is advantageously carried out with the use of a diluent. All inert solvents are suitable as diluents for carrying out the method of the invention. Named as examples are: halohydrocarbons, especially chlorohydrocarbons such as tetrachloroethylene, tetrachloroethane, dichloropropane, methylenechloride, dichlorobutane, chloroform, tetrachloromethane, trichloroethane, trichloroethylene, pentachloroethane, difluorobenzene, 1,2-dichloroethane, chlorobenzene, bromobenzene, dichlorobenzene, chlorotoluene, trichlorobenzene; alcohols such as methanol, ethanol, isopropanol, butanol; ethers such as ethylpropyl ether, methyl-tert-butyl ether, n-butyl ether, anisole, phenethol, cyclohexylmethyl ether, dimethyl ether, diethyl ether, dipropyl ether, diisopropyl ether, di-n-propyl ether, diisobutyl ether, diisoamyl ether, ethyleneglycol dimethyl ether, tetrahydrofuran, dioxan, dichlorodiethyl ether and polyethers of ethylene oxide and/or propylene oxide; amines such as trimethyl-, triethyl-, tripropyl-, tributylamine, N-methylmorpholin, pyridine and tetramethylenediamine, nitrohydrocarbons such as nitromethane, nitroethane, nitropropane, nitrobenzene, chloronitrobenzene, o-nitrotoluene; nitriles such as acetonitrile, propionitrile, butyronitrile, isobutyronitrile, benzonitrile, m-chlorobenzonitrile as well as compounds such as tetrahydrothiophene oxide and dimethylsulphoxide, tetramethylsulphoxide, dipropylsulphoxide, benzylmethylsulphoxide, diisobutylsulphoxide, dibutylsulphoxide, diisoamylsulphoxide; sulphones such as dimethyl-, diethyl-, dipropyl-, dibutyl-, diphenyl-, dihexyl-, methylhexyl-, ethylpropyl-, ethylisobutyl- and pentamethylenesulphone; aliphatic, cycloaliphatic or aromatic hydrocarbons, for example so-called white spirits with components with boiling points in the range of, for example, 40° C. to 250° C., cymol, petroleum fractions within a boiling range of 70° C. to 190° C., cyclohexane, methylcyclohexane, petroleum ether, ligroin, octane, benzene, toluene, chlorobenzene, bromobenzene, nitrotoluene, xylene; esters such as methyl, ethyl, butyl, isobutyl acetate as well as dimethyl, dibutyl, ethylene carbonate; amides such as hexamethylenephosphoric acid triamide, formamide, N-methylformamide, N,N-dimethylformamide, N,N-dipropylformamide, N,N-di-butylformamide, N-methylpyrrolidine, N-methylcaprolactam, 1,3-dimethyl 3,4,5,6-tetrahydro-2(1H)pyrimidine, octylpyrrolidine, octylcaprolactam, 1,3-dimethyl-2-imidazolindione, N-formylpiperidine, N,N'-1,4-diformylpiperazine; ketones such as acetone, acetophenone, methylethylketone, methylbutylketone.

Of course the method of the invention can also be carried out in mixtures of the named solvents or diluents.

When carrying out the method of the invention the reaction temperatures can be varied over a wide range. In general temperatures between −30° C. and +150° C., preferably between −10° C and +100° C., are used.

The method of the invention is generally carried out under normal pressure. However, it is possible to carry out the method of the invention under elevated or reduced pressure—generally between 0.1 and 15 bar.

In carrying out the method of the invention the starting materials are generally used in approximately equimolecular amounts. However, it is possible to use one of the components in a larger excess. In general the reaction is carried out in a suitable diluent in the presence of a reaction auxiliary, optionally also in a protective atmosphere (for example, under nitrogen, argon or helium) and generally the reaction mixture is stirred for several hours at the required temperature. Work-up is carried out by normal methods (cf. the preparation examples).

The active compounds of structure (I) of the invention are suitable for the protection of plants and plant organs, for increasing yields, improvement in quality of the produce and for the control of zoopests, especially insects, arachnids, helminths, nematodes and molluscs that occur in agriculture, horticulture, in animal breeding, in forestry, in garden and leisure facilities, in storage and material protection and in the hygiene sector with good plant tolerance, favourable mammalian toxicity and good environmental compatibility. They can be used preferably as plant protection agents. They are active against normal sensitive and resistant species as well as against all or individual developmental stages. The above named pests include:

the order Anoplura (Phthiraptera) e.g. *Damalinia* spp., *Haematopinus* spp., *Linognathus* spp., *Pediculus* spp., *Trichodectes* spp.

The class of Arachnida e.g. *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

The class of Bivalva e.g. *Dreissena* spp.

The order Chilopoda e.g. *Geophilus* spp., *Scutigera* spp.

The order Coleoptera e.g. *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

The order Collembola e.g. *Onychiurus armatus.*

The order Dermaptera e.g. *Forficula auricularia.*

The order Diplopoda e.g. *Blaniulus guttulatus.*

The order Diptera e.g. *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp. *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

The class Gastropoda e.g. *Arion* spp., *Biomphalaria* spp., *Bulinus* spp., *Deroceras* spp., *Galba* spp., *Lymnaea* spp., *Oncomelania* spp., *Succinea* spp.

The class of Helminths e.g. *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa loa, Nematodirus* spp., *Oesophagostomum* spp., *Opisthorchis* spp., *Onchocerca volvulus, Ostertagia* spp., *Paragonimus* spp., *Schistosomen* spp, *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

In addition protozoa such as Eimeria may be controlled.

The order Heteroptera e.g. *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

The order Homoptera e.g. *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Cameocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

The order Hymenoptera e.g. *Diprion* spp., *Hoplocampa* spp., *Lasius* spp., *Monomorium pharaonis, Vespa* spp.

The order Isopoda e.g. *Armadillidium vulgare, Oniscus asellus, Porcellio scaber.*

The order Isoptera e.g. *Reticulitermes* spp., *Odontotermes* spp.

The order Lepidoptera e.g. *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

The order Orthoptera e.g. *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

The order Siphonaptera e.g. *Ceratophyllus* spp., *Xenopsylla cheopis.*

The order Symphyla e.g. *Scutigerella immaculata.*

The order Thysanoptera e.g. *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

The order Thysanura e.g. *Lepisma saccharina.*

The plant parasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

The compounds of structure (I) of the invention are characterised particularly by strong action against aphids (e.g. *Aphis gossypii* and *Myzus persicae*), beetle larvae (e.g. *Phaedon cochleariae*), butterfly caterpillars (e.g. *Plutella xylostella, Spodoptera exigua* and *Spodoptera frugiperda*).

The compounds of the invention can optionally also be used in certain concentrations or application amounts as herbicides, safeners, growth regulators, or as agents for improving plant properties or as microbiocides, for example as fungicides, antimycotics, bactericides, viricides (including agents against viroids) or as agents against MLO (Mycoplasma-like organism) and RLO (Rickettsia-like organism). They may also be optionally used as intermediates or precursors for the synthesis of further active compounds.

According to the invention all plants and plant parts can be treated. Plants are hereby understood to mean all plants and plant populations such as desirable and undesirable wild plants or cultigens (including naturally occurring cultigens).

Cultigens can be plants that can be obtained by conventional breeding and optimisation methods or by biotechnology or genetic engineering methods or combinations of these methods, including transgenic plants and including plant varieties that are protectable or not protectable by plant varieties protection rights. Plant parts are understood to be all above ground and below ground parts and organs of the plants such as scion, leaf, blossom and root, including, for example, leaves, needles, stalks, stems, blossoms, fruiting bodies, fruits and seed as well as roots, bulbs, rhizomes. Harvest crops as well as vegetative and generative reproduction material, for example cuttings, bulbs, rhizomes, shoots and seed also belong to plant parts.

The treatment according to the invention of plants and plant parts with the active compound can be carried out directly or by action on their environment, habitat or storage facility by means of the normal treatment methods, for example, by immersion, spraying, evaporation, misting, scattering, painting, injecting, and with reproductive material, in particular with seed, also by single or multiple jacketing.

The active materials of the plants can be converted into the normal formulations such as solutions, emulsions, spray powders, water- and oil-based suspensions, powders, dusting agents, pastes, soluble powders, soluble granulates, spreading granulates, suspension-emulsion concentrates, active compound impregnated natural materials, active compound impregnated synthetic materials, fertilisers and microencapsulation in polymeric materials.

These formulations can be prepared by known methods, for example by mixing the active compound with diluents, that is solvents and/or solid carriers, optionally with the use of surfactants, that is emulsifiers and/or dispersants and/or foaming agents. The preparation of the formulations is carried out in suitable plants or also before or during use.

Materials that can be used as auxiliaries are those suitable to impart special properties on the material itself and/or preparations derived from it (e.g. spray emulsions, seed dressings) such as certain technical properties and/or special biological properties. Suitable auxiliaries are: diluents, solvents and carriers.

Suitable diluents are, for example, water, polar and non-polar organic liquids, for example from the class of aromatic and non-aromatic hydrocarbons (such as paraffin, alkylbenzenes, alkylnaphthalenes, chlorobenzenes), alcohols and polyols (that can be optionally substituted, etherified and/or esterified), ketones (such as acetone, cyclohexanone), esters (also fats and oils) and (poly)ethers, the simple and substituted amines, amides, lactams (such as N-alkylpyrrolidones) and lactones, sulphones and sulphoxides (such as dimethylsulphoxide).

Where water is used as diluent organic solvents, for example, can also be used as auxiliary solvents. Such suitable liquid solvents are essentially: aromatics such as xylene or toluene, or alkylnaphthalenes, chlorinated aromatics and chlorinated aliphatic hydrocarbons such as chlorobenzenes, chloroethylenes, methylene chloride, aliphatic hydrocarbons such as cyclohexane or paraffins, for example natural oil fractions, mineral and vegetable oils, alcohols such as butanol or glycol as well as their ethers and esters, ketones such as acetone, methylethylketone, methylisobutylketone or cyclohexanone, highly polar solvents such as dimethylsulphoxide, as well as water.

Suitable as solid carriers are:

for example, ammonium salts and natural mineral powders such a kaolin, clays, talc, chalk, quartz attapulgite, montmorillonite or diatomaceous earth, and synthetic mineral powders such as highly dispersed silica, aluminium oxide and silicates, suitable as carriers for granulates are: for example crushed and fractionated natural minerals such as calcite, marble, pumice, sepiolite, dolomite as well as synthetic granulates of inorganic and organic flours as well as granulates from organic materials such as paper, sawdust, coconut shells, maize ears and tobacco stalks; suitable as emulsifiers and foaming agents are; for example non-ionogenic and anionic emulsifiers such as polyoxyethylene fatty acid esters, polyoxyethylene fatty alcohol ethers, for example alkylarylpolyglycol ethers, alkylsulphonates, alkylsulphates, arylsulphonates and protein hydrolysates; suitable as dispersant are non-ionic and/or ionic materials, for example from the class of alcohol-POE and/or POP ethers, acid- and/or POP or POE esters, alkyl-aryl- and/or POP or POE ethers, fat- and/or POP or POE adducts, POE- and/or POP-polyol derivates, POE- and/or POP-sorbitan or sugar adducts, alkyl or aryl sulphates, sulphonates and phosphates or the respective PO ether adducts. In addition suitable oligo- or polymers, for example starting from vinylic monomers, of acrylic acid, from EO and/or PO alone or in combination with, for example (poly)alcohols or (poly)amines. In addition lignin and its sulphonic acid derivatives, simple and modified celluloses, aromatic and/or aliphatic sulphonic acids as well as their adducts with formaldehyde can be used.

Deposit builders such as carboxymethylcellulose, natural and synthetic powdery, granular or latex-like polymers can be used in the formulations, such as gum arabic, polyvinyl alcohol, polyvinyl acetate as well as natural phospholipids such a cephalins and lecithins and synthetic phospholipids.

Colouring agents such as inorganic pigments, for example iron oxide, titanium oxide, ferrocyanblue and organic colouring agents, such as alizarin, azo and metallophthalocyanin dyes and trace nutrients such as iron, manganese, boron, copper, cobalt, molybdenum and zinc salts can be used.

Further additives can be aromatic principles, mineral or vegetable, optionally modified, oils, waxes and nutrients (also trace nutrients) such as iron, manganese, boron, copper, cobalt, molybdenum and zinc salts.

Also included can be stabilisers such as cold stabilisers, preservatives, anti-oxidants, light-protectants or other chemical and/or physical agents for improving stability.

The formulations generally contain 0.01 and 98 wt. % active compound, preferably between 0.5 and 90%.

The active compound of the invention can be present in its normal commercial formulations or in application forms prepared from these formulations in admixture with other active compounds such as insecticides, attractants, sterilisers, bactericides, acaricides, nematicides, fungicides, growth regulators, herbicides, safeners, fertilisers or semiochemicals.

Particularly favourable mixing partners are, for example, the following:

Fungicides:

Nucleic Acid Synthesis Inhibitors
  benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid Inhibitors of Mitosis and Cell Division
  benomyl, carbendazim, diethofencarb, fuberidazole, pencycuron, thiabendazole, thiophanatemethyl, zoxamis Inhibitor of Respiratory Complex I
  diflumetorim Inhibitors of Respiratory Complex II
  boscalid, carboxin, fenfuram, flutolanil, furametpyr, mepronil, oxycarboxin, penthiopyrad, thifluzamide Inhibitor of Respiratory Complex III
  azoxystrobin, cyazofamide, dimoxystrobin, enestrobin, famoxadone, fenamidone, fluoxastrobin, kresoximmethyl, metominostrobin, orysastrobin, pyraclostrobin, picoxystrobin Decouplers
  dinocap, fluazinam Inhibitors of ATP Production
  fentin acetate, fentin chloride, fentin hydroxide, silthiofam Inhibitor of Amino Acid and Protein Biosynthesis
  andoprim, blasticidin-S, cyprodinil, kasugamycin, kasugamycin hydrochloride hydrate, mepanipyrim, pyrimethanil Inhibitors of Signal Transduction
  fenpiclonil, fludioxonil, quinoxyfen Inhibitors of Fat and Membrane Synthesis
  chlozolinate, iprodione, procymidone, vinclozolin
  ampropylfos, potassium ampropylfos, edifenphos, iprobenfos (IBP), isoprothiolane, pyrazophos
  tolclofos-methyl, biphenyl
  iodocarb, propamocarb, propamocarb hydrochloride Inhibitors of Ergosterol Biosynthesis
  fenhexamide,
  azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulphate, oxpoconazole, fenarimol, flurprimidol, nuarimol, pyrifenox, triforin, pefurazoate, prochloraz, triflumizole, viniconazole,
  aldimorph, dodemorph, dodemorph acetate, fenpropimorph, tridemorph, fenpropidin, spiroxamine,
  naftifin, pyributicarb, terbinafin Inhibitors of Cell Wall Synthesis
  benthiavalicarb, bialaphos, dimethomorph, flumorph, iprovalicarb, polyoxins, polyoxorim, validamycin A Inhibitors of Melanin Biosynthesis
  capropamide, diclocymet, fenoxanil, phtalide, pyroquilon, tricyclazole Resistance Induction
  acibenzolar-S-methyl, probenazole, tiadinil Multisite
  captafol, captan, chlorothalonil, copper salts: copper hydroxide, copper naphthenate, copper oxychloride, copper sulphate, copper oxide, oxine-copper and Bordeaux mixture, dichlofluanid, dithianon, dodin, dodin freie base, ferbam, fluorofolpet, guazatin, guazatin acetate, iminoctadin, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram Unknown Mechanism
  amibromdol, benthiazole, bethoxazin, capsimycin, carvone, quinoline methionate, chloropicrin, cufraneb, cyflufenamide, cymoxanil, dazomet, debacarb, diclomezine, dichlorophen, dicloran, difenzoquat, difenzoquat methyl sulphate, diphenylamine, ethaboxam, ferimzone, flumetover, flusulfamide, fluopicolide, fluoroimide, hexachlorobenzene, 8-hydroxyquinoline sulphate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosin-sodium, proquinazid, pyrrolnitrin, quintozen, tecloftalam, tecnazen, triazoxido, trichlamide, zarilamide and 2,3,5,6-tetrachloro-4-(methylsulphonyl)pyridine, N-(4-chloro-2-nitrophenyl)-N-ethyl-4-methylbenzene-sulphonamide, 2-amino-4-methyl-N-phenyl-5-thiazole carboxamide, 2-chloro-N-(2,3-dihydro-1,1,3-trimethyl-1H-inden-4-yl)-3-pyridine carboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)-phenyl]ethyliden]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridine dicarbonitriel, methyl 2-[[[cyclopropyl[(4-methoxyphenyl)imino]methyl]thio]methyl]-.alpha.-(methoxymethylen)-benzacetate, 4-chloro-alpha-propinyloxy-N-[2-[3-methoxy-4-(2-propinyloxy)phenyl]ethyl]-benzacetamide, (2S)-N-[2-[4-[[3-(4-chlorophenyl)-2-propinyl]oxy]-3-methoxyphenyl]ethyl]-3-methyl-2-[(methylsulphonyl)amino]-butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy) imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenylethyl)oxy]phenyl ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-Methoxy-3-pyridinyl)-cyclopropane carboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chlor-2-methylphenoxy)-5-fluoropyrimidin-4-yl]oxy}phenyl)-2-(methoxyimino)-N-methylacetamide Bactericides:

bronopol, dichlorophen, nitrapyrin, nickel dimethyldithiocarbamate, kasugamycin, octhilinon, furan carboxylic acid, oxytetracyclin, probenazol, streptomycin, tecloftalam, copper sulphate and other copper preparations.

Insecticide/Acaricide/Nematicide:

Acetylcholinesterase (AChE) Inhibitors
  carbamates,
    for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate
  organophosphates,
    for example acephate, azamethiphos, azinphos (-methyl, -ethyl), aromophos-ethyl, aromfenvinfos (-methyl), autathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphone, dialifos, diazinone, dichlofenthione, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidone, phosphocarb, Phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion Sodium Channel Modulators/Voltage-Dependent Sodium Channel Blockers
  pyrethroids,
    for example acrinathrin, allethrin (d-cis-trans, d-trans), beta-cyfluthrin, bifenthrin, bioallethrin, bioallethrin-S-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta), cyphenothrin, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, teralethrin, tetramethrin (−1R-isomer), tralomethrin, transfluthrin, ZXI 8901, pyrethrins (pyrethrum)
  DDT
  oxadiazines,
    for example indoxacarb Acetylcholine Receptor Agonists/Antagonists
  chloronicotinyls,
    for example acetamiprid, clothianidin, dinotefuran, imidacloprid, nitenpyram, nithiazine, thiacloprid, thiamethoxam
  nicotine, bensultap, cartap Acetylcholine Receptor Modulators
  Spinosynes,
    for example spinosad GABA Controlled Chloride Channel Antagonists
  Organochlorinee,
    for example camphechlor, chlordane, endosulfan, gamma-HCH, HCH, heptachlor, lindane, methoxychlor
  Fiproles,
    for example acetoprole, ethiprole, fipronil, pyrafluprole, pyriprole, vaniliprole Chloride Channel Activators
  Mectins,
    for example avermectin, emamectin, emamectin benzoate, ivermectin, milbemycin Juvenile Hormone Mimetics,
  for example diofenolan, epofenonane, fenoxycarb, hydroprene, kinoprene, methoprene, pyriproxifen, triprene Ecdysone agonists/disruptors
  diacylhydrazines,
    for example chromafenozide, halofenozide, methoxyfenozide, tebufenozide Inhibitors of Chitin Biosynthesis
  Benzoylureas,
    for example bistrifluron, chlofluazuron, diflubenzuron, fluazuron, flucycloxuron, flufenoxuron, hexaflumuron, lufenuron, novaluron, noviflumuron, penfluron, teflubenzuron, triflumuron
  buprofezin
  cyromazine Inhibitors of Oxidative Phosphorylation, ATP Disruptors
  diafenthiuron
  organotin compounds,
    for example azocyclotin, cyhexatin, fenbutatin-oxide Decouplers of Oxidative Phosphorylation by Interruption of H-Proton Gradients
  pyrrole,
    for example chlorfenapyr
  dinitrophenols,
    for example binapacyrl, dinobuton, dinocap, DNOC Site I Electron Transport Inhibitors
  METI's,
    for example fenazaquin, fenpyroximate, pyrimidifen, pyridaben, tebufenpyrad, tolfenpyrad
  hydramethylnon
  dicofol Site II Electron Transport Inhibitors
  rotenones Site III Electron Transport Inhibitors
  acequinocyl, fluacrypyrim Microbial Disruptors of Insect Intestinal Membrane
  *Bacillus thuringiensis* strains Inhibitors of Fat Synthesis
  tetramic acids,
    for example spirodiclofen, spiromesifen
  tetramic acids,
    for example spirotetramat (CAS-Reg.-No.: 203313-25-1) and 3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS-Reg.-No.: 382608-10-8)

carboxamides,
for example flonicamid
octopaminergic agonists,
for example amitraz Inhibitor of Magnesium-Stimulated ATPase,
propargite
benzoic acid dicarboxamides,
for example flubendiamide
Nereistoxin analogous,
for example thiocyclam hydrogen oxalate, thiosultap-sodium Biologicals, Hormones or Pheromones
azadirachtin, *Bacillus* spec., *Beauveria* spec., codlemone, *Metarrhizium* spec., *Paecilomyces* spec., thuringiensin, *Verticillium* spec.

Active Compounds with Unknown or Non-Specific Mode of Action
fumigants,
for example aluminium phosphide, methyl bromide, sulphuryl fluoride
feeding inhibitors,
for example cryolite, flonicamid, pymetrozine
mite growth inhibitors,
for example clofentezine, etoxazole, hexythiazox
amidoflumet, benclothiaz, benzoximate, bifenazate, bromopropylate, buprofezin, quinomethionate, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin A mixture with other known active compounds such as herbicides, fertilisers, growth regulators, safeners, semiochemicals or also with agents for improving plant properties is also possible.

The active compounds of the invention can also be present in their normal commercial formulations when used as insecticides as well as in the application forms prepared from these formulations in admixture with synergists. Synergists are compounds through which the activity of the active compound can be increased without the added synergist itself having to be active.

The active compounds of the invention can also be present in their normal commercial formulations when used as insecticides as well as in the application forms prepared from these formulations in admixture with inhibitors that reduce degradation of the active compound after use in the environment of the plants, on the surface of the plants or in plant tissues.

The active compound content of application forms prepared from the normal commercial formulations can vary over a wide range. The active compound content of the application form can lie within 0.00000001 to 95 wt. %, preferably between 0.00001 and 1 wt. %.

The application is carried out in a manner adapted to the application forms.

As previously described, according to the invention all plants and their parts can be treated. In a preferred embodiment wild or plant species and plant varieties obtained by conventional biological breeding methods such as crossing or protoplast fusion and their parts are treated. In a further preferred embodiment transgenic plants and plant varieties that were produced by genetic engineering methods optionally in combination with conventional methods (genetic modified organisms) and their parts are treated. The terms "parts" and "parts of plants" or "plant parts" were explained above.

Especially preferred according to the invention plants of the respective customary or generally used plant varieties are treated. Plant varieties are understood to mean plants with new properties ("traits") that have been bred by conventional breeding, by mutagenesis or by recombinant DNA techniques. These can be varieties, strains, bio- and genotypes.

Depending upon the plant species or plant varieties, their position and growth conditions (soil, climate, vegetation period, nutrition), superadditive ("synergistic") effects can occur by the treatment of the invention. Thus, for example, lower amounts of application and/or widening of the activity spectrum and/or increase in the action of the substances and agents that may be used according to the invention, improved plant growth, increased tolerance towards high or low temperatures, increased tolerance towards drought or towards water or soil salt content, increased blossoming performance, simplified harvesting, acceleration in ripening, increased harvest yields, higher quality and/or nutritional value of the harvested product, better storage life and/or processing of the harvested product are possible which extend beyond actually the expected effects.

All plants that have received by genetic engineering modification genetic material that imparts particularly advantageous valuable properties ("traits") to these plants belong to the transgenic (obtained by genetic engineering) plants or plant varieties to be preferably treated in accordance with the invention. Examples of such properties are improved plant growth, increased tolerance toward high or low temperatures, increased tolerance toward drought or toward water or soil salt content, improved blossoming performance, simplified harvesting, accelerated ripening, increased harvest yields, improved quality and/or nutritional value of the crop, better storage life and/or processing of the crop. Further and particularly emphasised examples of such properties are increased resistance of the plants toward zoopests and microbial pests, such as toward insects, mites, pathogenic plant fungi, bacteria and/or viruses as well as an increased tolerance of the plants toward certain herbicides. Examples of such transgenic plants are the important cultigens such as cereals (wheat, rice), maize, soy, potato, sugar beet, tomato, peas, and other vegetable varieties, cotton, tobacco, rape as well as fruit plants (with the fruits apple, pear, citrus fruits and grapes), whereby maize, soy, potato, cotton, tobacco and rape are especially emphasised. Properties ("traits") especially emphasised are the increased tolerance of the plants toward insects, arachnids, nematodes and gastropods through the toxins formed in the plants, especially those that are produced in the plants (hereinafter known as "Bt plants") by the genetic material from *Bacillus thuringiensis* (e.g. from the genes CryIA(a), CryIA(b), CryIA(c), CryIIA, CryIIIA, CryIIIB2, Cry9c Cry2Ab, Cry3Bb and CryIF as well as their combinations). Also particularly emphasised as properties ("traits") is the increased resistance of plants toward fungi, bacteria and viruses through systemically acquired resistance (SAR), systemin, phytoalexine, elicitors and resistance genes and correspondingly expressed proteins and toxins. Further particularly emphasised properties ("traits") are the increased tolerance of the plants to certain active herbicidal compounds, for example imidazolinones, sulphonylureas, glyphosate or phosphinotricin (e.g. "PAT"-gene). The respective genes imparting the desired properties ("traits") can also occur in the transgenic plants in combination with each other. Examples of such "Bt plants" are maize varieties, cotton varieties, soy varieties and potato varieties that are marketed under the trade marks YIELD GARD® (e.g. maize, cotton, soy), KnockOut® (e.g. maize), StarLink® (e.g. maize), Bollgard® (cotton), Nucotn® (cotton) and NewLeaf® (potato). Examples of herbicide tolerant plants are maize varieties, cotton varieties and soy varieties that are marketed under the trade marks Roundup Ready® (tolerance toward glyphosate, e.g. maize, cotton, soy), Liberty Link® (tolerance toward phosphinotricin, e.g. rape), IMI® (tolerance toward imidazolinones) and STS® (tolerance toward sulphonyl ureas, e.g. maize). Also mentioned as herbicide resistant (conventionally bred for herbicide tolerance) plants are those varieties marketed under the name Clearfield® (e.g. maize). Naturally these statements also apply to plant varieties developed or marketed in the future with these genetic properties ("traits") or those developed in the future.

According to the invention the plants described can be particularly advantageously treated with the compounds of general structure I or active compound mixtures of the invention. The preferred ranges described above for the active compounds or mixtures hold also for the treatment of these plants. Particularly mentioned is plant treatment with the compounds or mixtures specially described in the present text.

The compounds of the invention are not only active against plant, hygiene and storage pests but also against zoopests in the veterinary sector (ectoparasites and endoparasites) such as hard ticks, soft ticks, mange ticks, harvest mites, flies (stinging and licking), parasitic fly larvae, lice, biting mites, chewing mites and fleas. These parasites include:

The order Anoplurida e.g. *Haematopinus* spp., *Linognathus* spp., *Pediculus* spp., *Phtirus* spp., *Solenopotes* spp.

The order Mallophagida and the suborders Amblycerina and Ischnocerina e.g. *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

The order Diptera and the suborders Nematocerina and Brachycerina e.g. *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

The order Siphonapterida e.g. *Pulex* spp., *Ctenocephalides* spp., *Xenopsylla* spp., *Ceratophyllus* spp.

The order Heteropterida e.g. *Cimex* spp., *Triatoma* spp., *Rhodnius* spp., *Panstrongylus* spp.

The order Blattarida e.g. *Blatta orientalis*, *Periplaneta americana*, *Blattela germanica*, *Supella* spp.

The subclass Acari (Acarina) and the order Meta- and Mesostigmata e.g. *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

The order Actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The compounds of the invention of structure (I) are also suitable for the control of arthropods that affect agricultural animals such as cattle, sheep, goats, horses, pigs, donkeys, camels, buffalo, rabbits, chickens, turkeys, ducks, geese, bees, other domestic animals such as dogs, cats, cage birds, aquarium fish as well as so-called experimental animals such as hamsters, guinea pigs, rats and mice. By control of these arthropods death rates and performance loss (in meat, milk, wool, hides, eggs, honey, etc.) will be reduced so that a more economic and simpler animal husbandry is possible by the use of the compounds of the invention.

The use of the active compounds in veterinary sector and animal husbandry is carried out by known means by enteric administration in the form of, for example, tablets, capsules, drinks, drenches, granulates, pastes, boli, the feed-through process, suppositories, by parenteral administration by, for example, injection (intramuscular, subcutaneous, intravenous, interperitoneal, among others), implants, by nasal application, by dermal administration in the form of, for example, dipping, spraying, pour-on and spot-on, washing, powdering and with the help of appliances containing the active compound such as collars, ear markers, tail markers, limb bands, halters, marking devices, etc.

During use in cattle, poultry, domestic animals, etc., the active compounds of structure (I) can be used as formulations (for example, powder, emulsions, flowable agents) that contain the active compounds in an amount of 1 to 80 wt. %, directly or after 100 to 10,000 times dilution or as a chemical bath.

Moreover it has been found that the compounds of the invention exhibit high insecticidal action against insects that destroy technical materials.

As example and preferably—but not limiting—the following insects are named:

Beetles such as *Hylotrupes bajulus*, *Chlorophorus pilosis*, *Anobium punctatum*, *Xestobium rufovillosum*, *Ptilinus pecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthes rugicollis*, *Xyleborus* spec. *Tryptodendron* spec. *Apate monachus*, *Bostrychus capucins*, *Heterobostrychus brunneus*, *Sinoxylon* spec. *Dinoderus minutus*;

Hymenoptera such as *Sirex juvencus*, *Urocerus gigas*, *Urocerus gigas taignus*, *Urocerus augur*;

Termites such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis*, *Coptotermes formosanus*;

Silverfish such as *Lepisma saccharina*.

Within the present context technical materials are understood to mean non-living materials such as preferably plastics, adhesives, glues, paper and cardboard, leather, wood, wood fabrication products and paints.

The ready-to-use agents can optionally include further insecticides and optionally one or more fungicides.

In respect of possible mixing partners reference is made to the above-named insecticides and fungicides.

At the same time the compounds of the invention can be used for protection against fouling of objects, especially ships' hulls, screens, nets, buildings, wharfs and signal installations that come into contact with sea or brackish water.

Moreover, the compounds of the invention can be used in combination with other active compounds as anti-fouling agents.

The active compounds are suitable for the control of zoopests in household, hygiene and storage protection, especially insects, arachnids and mites that appear in enclosed spaces such as apartments, factory halls, offices, vehicle cabins, etc.

They can be used alone or in combination with other active compounds and auxiliaries in household insecticidal products for the control of these pests. They are active against sensitive and resistant species as well as against all development stages. These pests include:

The order Scorpionidea e.g. *Buthus occitanus.*

The order Acarina e.g. *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

The order Araneae e.g. *Aviculariidae, Araneidae.*

The order Opiliones e.g. *Pseudoscorpiones chelifer, Pseudoscorpiones cheiridium, Opiliones phalangium.*

The order Isopoda e.g. *Oniscus asellus, Porcellio scaber.*

The order Diplopoda e.g. *Blaniulus guttulatus, Polydesmus* spp.

The order Chilopoda e.g. *Geophilus* spp.

The order Zygentoma e.g. *Ctenolepisma* spp., *Lepisma saccharina, Lepismodes inquilinus.*

The order der Blattaria e.g. *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

The order Saltatoria e.g. *Acheta domesticus.*

The order Dermaptera e.g. *Forficula auricularia.*

The order Isoptera e.g. *Kalotermes* spp., *Reticulitermes* spp.

The order Psocoptera e.g. *Lepinatus* spp., *Liposcelis* spp.

The order Coleoptera e.g. *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

The order Diptera e.g. *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

The order Lepidoptera e.g. *Achroia grisella, Galleria mellonella, Plodia interpunctella, Tinea cloacella, Tinea pellionella, Tineola bisselliella.*

The order Siphonaptera e.g. *Ctenocephalides canis, Ctenocephalides felis, Pulex irritans, Tunga penetrans, Xenopsylla cheopis.*

The order Hymenoptera e.g. *Camponotus herculeanus, Lasius fuliginosus, Lasius niger, Lasius umbratus, Monomorium pharaonis, Paravespula* spp., *Tetramorium caespitum.*

The order Anoplura e.g. *Pediculus humanus capitis, Pediculus humanus corporis, Pemphigus* spp., *Phylloera vastatrix, Phthirus pubis.*

The order Heteroptera e.g. *Cimex hemipterus, Cimex lectularius, Rhodinus prolixus, Triatoma infestans.*

The use in the household insecticidal sector is carried out alone or in combination with other suitable active compounds such as phosphates, carbamates, pyrethroids, neonicotinoids, growth regulators or active compounds from other known classes of insecticides.

Use is carried out with aerosols, non-pressurised spray agents, e.g. pump and dusting sprays, nebulisers, misters, foamers, gels, evaporation products with evaporation platelets of cellulose or plastic, liquid evaporators, gel and membrane evaporators, propeller-driven evaporators, non-energy or passive evaporation systems, fly papers, fly traps, and fly gels, as granulates or dusts, in scatter bait or bait stations.

PREPARATION EXAMPLES

Example 1

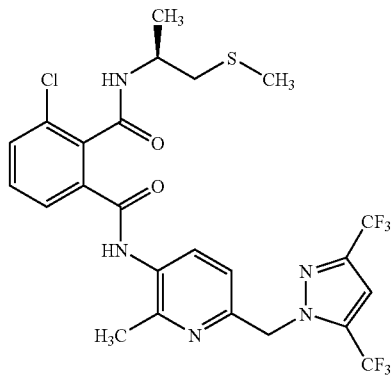

0.80 g (2.47 mmol) 6-{[3,5-bis(trifluoromethyl)-1H-pyrazol-1-yl]methyl}-2-methylpyridine-3-amine are dissolved in 8 ml 1,2-dichlorethane, treated with 4 drops of concentrated hydrochloric acid and heated to 55° C. A solution of 0.93 g (3.45 mmol) (3Z)-4-chloro-3-{[(1S)-1-methyl-2-(methylthio)ethyl]imino}-2-benzofuran-1(3H)-one in 6 ml 1,2-dichlorethane is added and the mixture stirred for 30 minutes at 65° C. The solvent is then distilled off under reduced pressure and the residue is purified by chromatography on silica with 1) dichloromethane and 2) cyclohexane/ethyl acetate 2:1 as eluents.

0.56 g (37% of theory) $N^1$-(6-{[3,5-bis(trifluoromethyl)-1H-pyrazol-1-yl]methyl}-2-methylpyridin-3-yl)-3-chloro-$N^2$-[(1S)-1-methyl-2-(methylthio)ethyl]phthalamide is obtained as yellow solid of melting point 92° C.

Example 2

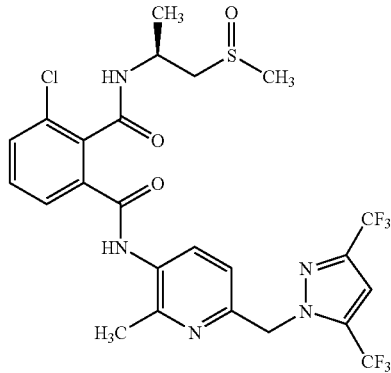

(Subsequent Conversion)

0.21 g (0.35 mmol) $N^1$-(6-{[3,5-bis(trifluoromethyl)-1H-pyrazol-1-yl]methyl}-2-methylpyridin-3-yl)-3-chloro-$N^2$-[(1S)-1-methyl-2-(methylthio)ethyl]phthalamide are dissolved in 5 ml 1,2-dichloroethane and 3.3 mg (0.07 mmol) formic acid and 44.1 mg (0.39 mmol) hydrogen peroxide are added sequentially at 60° C. and the mixture is stirred for 30 min at 60° C. The reaction mixture is treated with stirring with 5 ml of a 10% sodium hydrogen sulphite solution (bisulphite) at 50° C., stirred for 10 minutes and quenched with 10 ml of a 10% sodium hydrogen carbonate solution. The organic phase is separated and the aqueous phase extracted twice with dichloromethane. The combined organic phases are dried over sodium sulphate and after distillation of the solvent under reduced pressure the product is obtained as a white solid.

0.20 g (86% of theory) $N^1$-(6-{[3,5-bis(trifluoromethyl)-1H-pyrazol-1-yl]methyl}-2-methylpyridin-3-yl)-3-chloro-$N^2$-[(1S)-1-methyl-2-(methylsulphinyl)ethyl]phthalamide of melting point 183° C. is obtained.

Example 3

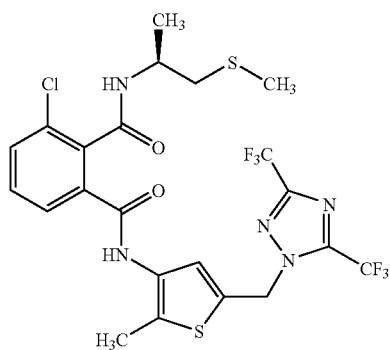

0.39 g (1.18 mmol) 5-{[3,5-bis(trifluoromethyl)-1H-1,2,4-triazol-1-yl]methyl}-2-methylthiophene-3-amine are dissolved in 8 ml 1,2-dichloroethane, 3 drops of concentrated hydrochloric acid are added. The mixture is heated to 55° C., a solution of 382 mg (1.42 mmol) (3Z)-4-chloro-3-{[(1S)-1-methyl-2-(methylthio)ethyl-imino}-2-benzofuran-1(3H)-one in 6 ml 1,2-dichloroethane is added and the mixture is stirred at 65° C. for 30 minutes. The solvent is then distilled off under reduced pressure and the residue is purified further by preparative HPLC.

44 mg (6% of theory) $N^1$-(5-{[3,5-bis(trifluoromethyl)-1H-1,2,4-triazol-1-yl-methyl}-2-methyl-3-thienyl)-3-chloro-$N^2$-[(1S)-1-methyl-2-(methylthio)ethyl]phthalamide is obtained.

HPLC: log P (pH 2.3)=3.8

Example 4

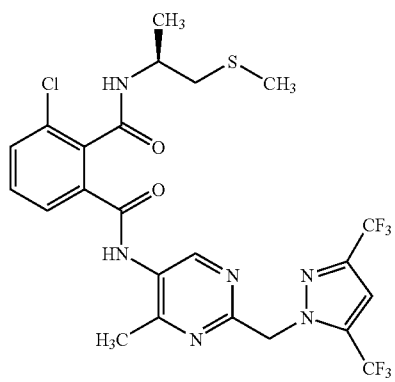

To a solution of 435 mg (1.61 mmol) 4-chloro-3-(S-1-methyl-2-methylsulphanylethylimino)-3H-isobenzofuran-1-one in 5 ml 1,2-dichloroethane are added sequentially 500 mg (1.53 mmol) 2-(3,5-bistrifluoromethylpyrazol-1-ylmethyl)-4-methylpyrimidin-5-ylamine and 7.3 mg (38 mmol) p-tolu-ene-sulphonic acid monohydrate and the mixture is then heated for 2 hours at 50° C. After cooling to room temperature the residue is purified on silica with cyclohexane/ethyl acetate 3:1→2:1 as eluent.

0.90 g (96% of theory) $N^1$-[2-(3,5-bis-trifluoromethyl-pyrazol-1-ylmethyl)-4-methylpyrimidin-5-yl]-3-chloro-$N^2$-(S-1-methyl-2-methylsulphanylethyl)phthalamide are obtained as colourless solid.

HPLC: log P (pH 2.3)=3.39

Example 5

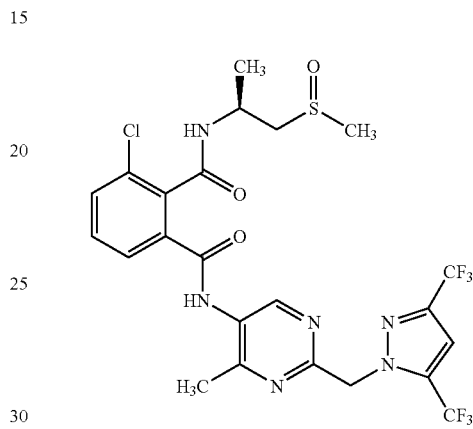

To a solution of 300 mg (0.50 mmol) $N^1$-[2-(3,5-bistrifluoromethylpyrazol-1-ylmethyl)-4-methylpyrimidin-5-yl]-3-chloro-$N^2$-(S-1-methyl-2-methylsulphanylethyl)phthalamide in 3 ml chloroform at 0° C. is added slowly a solution of 127 mg (0.55 mmol) meta-chloroperbenzoic acid (75% in water) in 3 ml chloroform. The reaction mixture is allowed to warm to room temperature over 1.5 h and is then heated at 40° C. for 30 min. After cooling to room temperature the reaction mixture is diluted with dichloromethane and sequentially washed with 10% sodium hydroxide and sat. NaCl solution and dried over sodium sulphate. After removal of the solvent the residue is purified by chromatography on silica with dichloromethane/methanol 10:1 as eluent.

30 mg (9% of theory) $N^1$-[2-(3,5-bistrifluoromethylpyrazol-1-ylmethyl)-4-methylpyrimidin-5-yl]-3-chloro-$N^2$-(S-2-methanesulphinyl-1-methylethyl)phthalamide is obtained as colourless solid.

HPLC: log P (pH 2.3)=2.17

Analogous to examples 1 to 5 and in accordance with the general description of the preparation methods of the invention the compounds listed in Table 1 of structure (I) and structure (IA) can for example also be prepared.

(IA)

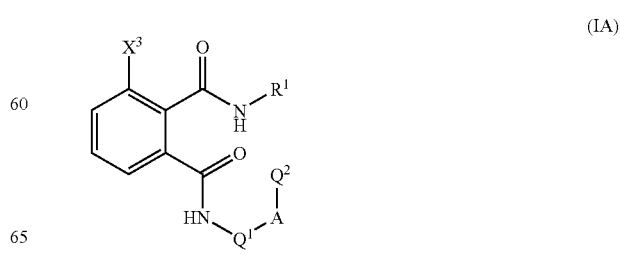

TABLE 1

Examples of compounds of structure (IA)

| Ex. no. | A | Q¹ | Q² | R¹ | X³ | Physical data |
|---|---|---|---|---|---|---|
| 6 | $CH_2$ | (NH), 3-amino-2,6-dimethylpyridine | 3,5-bis(CF₃)-1-methylpyrazole | $CH_3$, $CH(CH_3)CH_2SCH_3$ | I | log P (pH 2.3): 3.68 |
| 7 | $CH_2$ | (NH), 3-amino-2,6-dimethylpyridine | 3,5-bis(CF₃)-1-methylpyrazole | $CH_3$, $CH(CH_3)CH_2S(O)CH_3$ | I | log P (pH 2.3): 2.42 |
| 8 | $CH_2$ | (NH), 3-amino-2,6-dimethylpyridine | 3,5-bis(CF₃)-1-methylpyrazole | $CH_3$, $CH(CH_3)CH_2S(O)_2CH_3$ | I | log P (pH 2.3): 2.80 |
| 9 | $CH_2$ | (NH), 3-amino-2,6-dimethylpyridine | 3,5-bis(CF₃)-1-methylpyrazole | $CH_3$, $CH(CH_3)CH_2S(O)_2CH_3$ | Cl | log P (pH 2.3): 2.69 |
| 10 | $CH_2$ | (NH), 3-amino-2,6-dimethylpyridine | 3,5-bis(CF₃)-1-methylpyrazole | $CH_3$, $CH(CH_3)CH_2SCH_3$ | Br | log P (pH 2.3): 3.59 |
| 11 | $CH_2$ | (NH), 3-amino-2,6-dimethylpyridine | 3,5-bis(CF₃)-1-methylpyrazole | $CH_3$, $CH(CH_3)CH_2S(O)CH_3$ | Br | log P (pH 2.3): 2.32 |
| 12 | $CH_2$ | (NH), 3-amino-2,6-dimethylpyridine | 3,5-bis(CF₃)-1-methyl-1,2,4-triazole | $CH_3$, $CH(CH_3)CH_2SCH_3$ | I | log P (pH 2.3): 3.52 |
| 13 | $CH_2$ | (NH), 3-amino-2,6-dimethylpyridine | 3,5-bis(CF₃)-1-methyl-1,2,4-triazole | $CH_3$, $CH(CH_3)CH_2S(O)CH_3$ | I | log P (pH 2.3): 2.28 |

TABLE 1-continued

Examples of compounds of structure (IA)

| Ex. no. | A | Q¹ | Q² | R¹ | X³ | Physical data |
|---|---|---|---|---|---|---|
| 14 | CH₂ | (NH) 3-amino-2-methylpyridine | 3,5-bis(CF₃)-1-methyl-1,2,4-triazole | CH₃CH(CH₂SCH₃) | Cl | log P (pH 2.3): 3.39 |
| 15 | CH₂ | (NH) 3-amino-2-methylpyridine | 3,5-bis(CF₃)-1-methyl-1,2,4-triazole | CH₃CH(CH₂S(O)CH₃) | Cl | log P (pH 2.3): 2.17 |
| 16 | CH₂ | (NH) 3-amino-2-methylpyridine | 3,5-bis(CF₃)-1-methyl-1,2,4-triazole | CH₃CH(CH₂S(O)₂CH₃) | Cl | log P (pH 2.3): 2.56 |
| 17 | CH₂ | (NH) 3-amino-2-methylpyridine | 3,5-bis(CF₃)-1-methyl-pyrazole | CH₃CH(CH₂SCH₃) | Br | log P (pH 2.3): 3.44 |
| 18 | CH₂ | (NH) 5-amino-4-methylpyrimidine | 3,5-bis(CF₃)-1-methyl-pyrazole | CH₃CH(CH₂SCH₃) | Br | log P (pH 2.3): 3.44 |
| 19 | CH₂ | (NH) 5-amino-4-methylpyrimidine | 3,5-bis(CF₃)-1-methyl-pyrazole | CH₃CH(CH₂SCH₃) | I | log P (pH 2.3): 3.55 |
| 20 | CH₂ | (NH) 5-amino-4-methylpyrimidine | 3,5-bis(CF₃)-1-methyl-1,2,4-triazole | CH₃CH(CH₂SCH₃) | Cl | log P (pH 2.3): 3.24 |
| 21 | CH₂ | (NH) 5-amino-4-methylpyrimidine | 3,5-bis(CF₃)-1-methyl-1,2,4-triazole | CH₃CH(CH₂SCH₃) | Br | log P (pH 2.3): 3.29 |

TABLE 1-continued
Examples of compounds of structure (IA)
| Ex. no. | A | Q¹ | Q² | R¹ | X³ | Physical data |
|---|---|---|---|---|---|---|
| 22 | CH₂ | 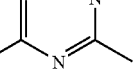 | 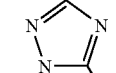 | 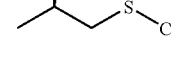 | I | log P (pH 2.3): 3.35 |
| 23 | CH₂ | 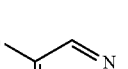 | 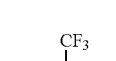 | 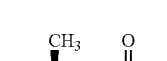 | Br | log P (pH 2.3): 2.20 |
| 24 | CH₂ | 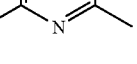 | 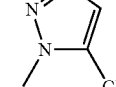 |  | I | log P (pH 2.3): 2.27 |
| 25 | CH₂ | 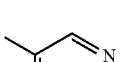 | 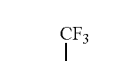 |  | Cl | log P (pH 2.3): 3.29 |
| 26 | CH₂ | 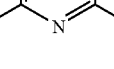 | 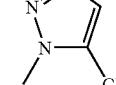 |  | Cl | log P (pH 2.3): 2.91 |
| 27 | CH₂ | 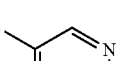 | 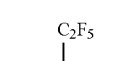 | 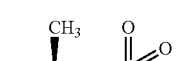 | Cl | log P (pH 2.3): 4.11 |
| 28 | CH₂ | 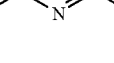 | 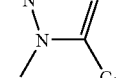 |  | Br | log P (pH 2.3): 2.42 |
| 29 | CH₂ | 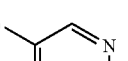 | 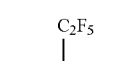 | 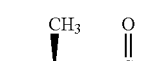 | Cl | log P (pH 2.3): 2.41 |

TABLE 1-continued
Examples of compounds of structure (IA)
| Ex. no. | A | Q$^1$ | Q$^2$ | R$^1$ | X$^3$ | Physical data |
|---|---|---|---|---|---|---|
| 30 | CH$_2$ | (NH)  |  |  | Cl | log P (pH 2.3): 3.62 |
| 31 | CH$_2$ | (NH)  |  |  | Br | log P (pH 2.3): 3.67 |
| 32 | CH$_2$ | (NH)  |  |  | Cl | log P (pH 2.3): 1.67 |
| 33 | CH$_2$ | (NH)  |  |  | Cl | log P (pH 2.3): 1.89 |
| 34 | CH$_2$ | (NH)  |  |  | Cl | log P (pH 2.3): 2.56 |
| 35 | CH$_2$ | (NH)  |  |  | Cl | log P (pH 2.3): 2.65 |
| 36 | CH$_2$ | (NH)  |  |  | Br | log P (pH 2.3): 2.07 |
| 37 | CH$_2$ | (NH)  |  |  | Br | log P (pH 2.3): 2.49 |

TABLE 1-continued
Examples of compounds of structure (IA)
| Ex. no. | A | Q¹ | Q² | R¹ | X³ | Physical data |
|---|---|---|---|---|---|---|
| 38 | CH₂ | 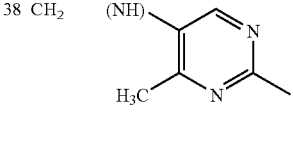 | 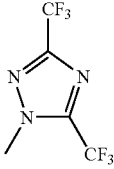 | 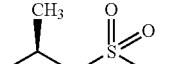 | Cl | log P (pH 2.3): 2.42 |
| 39 | CH₂ | 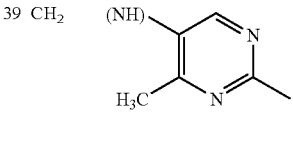 | 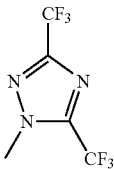 | 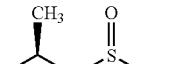 | Cl | log P (pH 2.3): 2.11 |
| 40 | CH₂ | 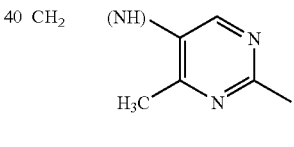 | 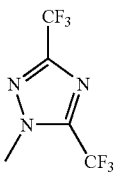 | 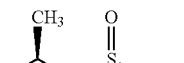 | I | log P (pH 2.3): 2.13 |
| 41 | CH₂ | 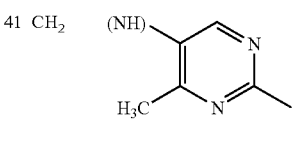 | 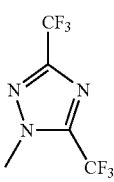 | 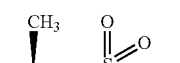 | I | log P (pH 2.3): 2.54 |
| 42 | CH₂ | 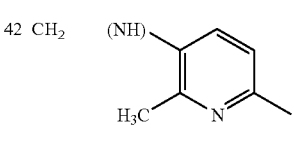 | 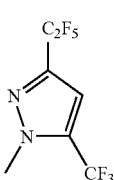 |  | Cl | log P (pH 2.3): 3.95 |
| 43 | CH₂ | 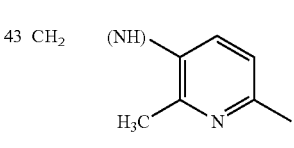 | 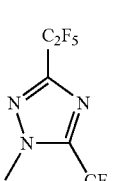 |  | Cl | log P (pH 2.3): 3.80 |
| 44 | CH₂ | 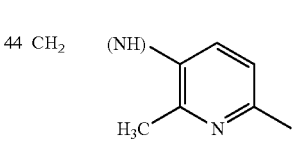 | 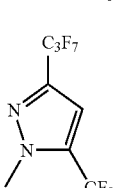 |  | Cl | log P (pH 2.3): 4.37 |
| 45 | CH₂ | 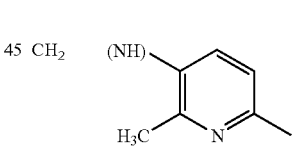 | 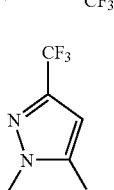 | 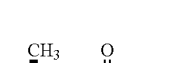 | Br | log P (pH 2.3): 2.76 |

TABLE 1-continued

Examples of compounds of structure (IA)

| Ex. no. | A | Q¹ | Q² | R¹ | X³ | Physical data |
|---|---|---|---|---|---|---|
| 46 | CH₂ | (NH) 2-methyl-6-methyl-pyridin-3-yl | 1-methyl-3-C₂F₅-4-CF₃-5-F-pyrazol-yl | (S)-CH(CH₃)CH₂SCH₃ | Cl | log P (pH 2.3): 4.15 |
| 47 | CH₂ | (NH) 2-methyl-6-methyl-pyridin-3-yl | 1-methyl-3-C₂F₅-5-C₂F₅-1,2,4-triazol-yl | (S)-CH(CH₃)CH₂SCH₃ | Cl | log P (pH 2.3): 4.23 |
| 49 | CH₂ | (NH) 2-methyl-6-methyl-pyridin-3-yl | 1-methyl-3-C₂F₅-5-C₂F₅-pyrazol-yl | (S)-CH(CH₃)CH₂SCH₃ | Cl | log P (pH 2.3): 4.37 |
| 50 | CH₂ | (NH) 2-methyl-6-methyl-pyridin-3-yl | 1-methyl-3-CHF₂-5-CHF₂-pyrazol-yl | (S)-CH(CH₃)CH₂SCH₃ | Cl | log P (pH 2.3): 2.88 |
| 51 | CH₂ | (NH) 2-methyl-6-methyl-pyridin-3-yl | 1-methyl-3-CF₃-5-CF₃-1,2,4-triazol-yl | (S)-CH(CH₃)CH₂S(O)₂CH₃ | Br | log P (pH 2.3): 2.70 |
| 52 | CH₂ | (NH) 2-methyl-6-methyl-pyridin-3-yl | 1-methyl-3-CF₃-5-CF₃-1,2,4-triazol-yl | (S)-CH(CH₃)CH₂S(O)₂CH₃ | I | log P (pH 2.3): 2.74 |
| 53 | CH₂ | (NH) 2-methyl-6-methyl-pyridin-3-yl | 1-methyl-3-CF₃-5-CF₃-1,2,4-triazol-yl | (S)-CH(CH₃)CH₂S(O)CH₃ | Br | log P (pH 2.3): 2.29 |
| 54 | CH₂ | (NH) 2-methyl-6-methyl-pyridin-3-yl | 1-methyl-3-C₂F₅-5-C₂F₅-1,2,4-triazol-yl | (S)-CH(CH₃)CH₂S(O)CH₃ | Cl | log P (pH 2.3): 2.98 |

TABLE 1-continued
Examples of compounds of structure (IA)
| Ex. no. | A | Q¹ | Q² | R¹ | X³ | Physical data |
|---|---|---|---|---|---|---|
| 55 | CH$_2$ | 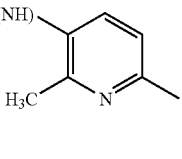 | 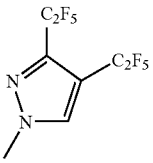 | 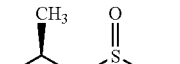 | Cl | log P (pH 2.3): 3.04 |
| 56 | CH$_2$ | 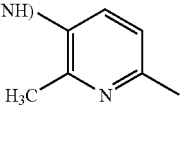 | 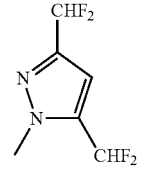 | 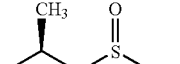 | Cl | log P (pH 2.3): 1.89 |
| 57 | CH$_2$ | 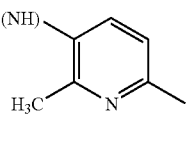 | 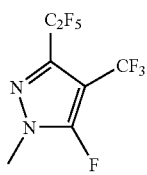 | 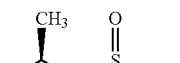 | Cl | log P (pH 2.3): 2.88 |
| 58 | CH$_2$ | 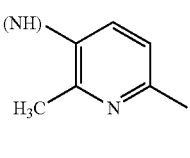 | 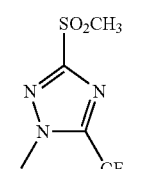 | 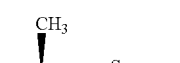 | Cl | log P (pH 2.3): 2.51 |
| 59 | CH$_2$ | 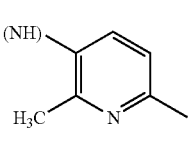 | 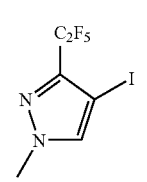 |  | Cl | log P (pH 2.3): 3.60 |
| 60 | CH$_2$ | 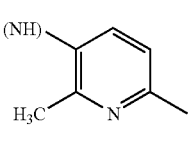 | 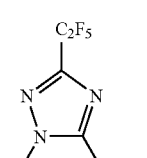 | 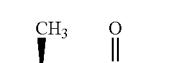 | Cl | log P (pH 2.3): 3.02 |
| 61 | CH$_2$ | 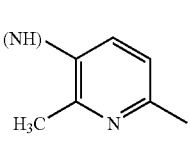 | 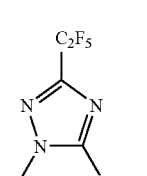 | 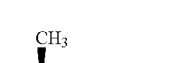 | Cl | log P (pH 2.3): 3.33 |
| 62 | CH$_2$ | 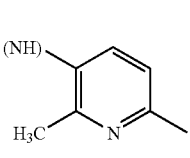 | 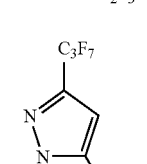 | 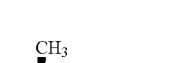 | Cl | log P (pH 2.3): 4.47 |

TABLE 1-continued

Examples of compounds of structure (IA)

| Ex. no. | A | $Q^1$ | $Q^2$ | $R^1$ | $X^3$ | Physical data |
|---|---|---|---|---|---|---|
| 63 | $CH_2$ | (NH)-1-methyl-3-methylpyrazol-5-yl | 1-methyl-3,5-bis(CF$_3$)pyrazol-4-yl | (S)-CH(CH$_3$)CH$_2$SCH$_3$ | Cl | log P (pH 2.3): 3.22 |
| 64 | $CH_2$ | (NH)-2-methylpyrimidin-5-yl (4-CH$_3$) | 1-methyl-3,4-bis(C$_2$F$_5$)pyrazol-5-yl | (S)-CH(CH$_3$)CH$_2$SCH$_3$ | Cl | log P (pH 2.3): 4.11 |
| 65 | $CH_2$ | (NH)-2-methylpyrimidin-5-yl (4-CH$_3$) | 1-methyl-3,4-bis(C$_2$F$_5$)pyrazol-5-yl | (S)-CH(CH$_3$)CH$_2$S(O)CH$_3$ | Cl | log P (pH 2.3): 2.91 |
| 66 | $CH_2$ | (NH)-2-methylpyrimidin-5-yl (4-CH$_3$) | 1-methyl-3,4-bis(C$_2$F$_5$)pyrazol-5-yl | (S)-CH(CH$_3$)CH$_2$S(O)$_2$CH$_3$ | Cl | log P (pH 2.3): 3.29 |

The determination of the log P values given in the above table and preparation examples is carried out in accordance with EEC directive 79/831 Annex V.A8 by HPLC (High Performance Liquid Chromatography) on a reverse phase column (C 18). Temperature: 43° C.

The determination is carried out under acidic conditions at pH 2.3 with 0.1% aqueous phosphoric acid and acetonitrile as eluents; linear gradient of 10% acetonitrile to 95% acetonitrile.

The determination with LC-MS under acidic conditions is carried out at pH 2.7 with 0.1% aqueous formic acid and acetonitrile (contains 01% formic acid) as eluents; linear gradient from 10% acetonitrile to 95% acetonitrile.

The determination of the LC-MS under neutral conditions is carried out at pH 7.8 with 0.001 molar aqueous ammonium hydrogen carbonate solution and acetonitrile as eluents; linear gradient of 10% acetonitrile to 95% acetonitrile.

Calibration was is carried out with unbranched alkan-2-ones (with 3 to 16 carbon atoms) of known log P values (Determination of log P values by the retention times by linear interpolation between two sequential alkanones).

The lambda max values were determined by UV spectra of 200 nm to 400 nm in the maxima of chromatographic signals.

Preparation of Starting Materials of Structure (II)

Example (II-1)

Stage 1

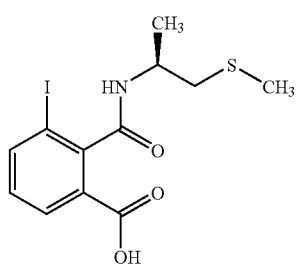

34.7 g (127 mmol) 3-iodophthalic anhydride are dissolved in N,N-dimethylacetamide and at 10° C. a solution of 16.0 g (152 mmol) (S)-1-methyl-2-methylsulphanylethylamine in N,N-dimethylacetamide is added over 60 minutes. The mixture is stirred for a further 60 minutes. A solution of 16.5 g (165 mmol) sodium hydroxide in water is then added over 70 minutes and the mixture is stirred for a further 12 hours. The solvent is distilled of under reduced pressure, the residue is mixed with water and tert-butylmethyl ether and adjusted to pH=1-2 with hydrochloric acid. The organic phase is separated, washed with water and then with saturated sodium chloride solution, dried with sodium sulphate and filtered. The solvent is carefully distilled from the filtrate under reduced pressure. The initially oily product usually crystallises within a few hours.

22.3 g (46% of theory) 3-iodo-N-[(S)-(1-methyl-2-methylsulphanylethyl)phthalamic acid of melting point 132-134° C. are obtained.

Stage 2

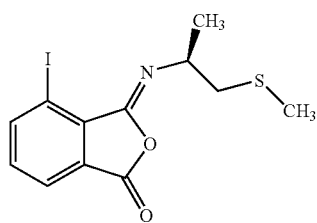

15.1 g (38.8 mmol) 3-Iodo-N-[(S)-1-methyl-2-methylsulphanylethyl]phthalamic acid are dissolved in dichloromethane. 6.02 g (71.7 mmol) sodium hydrogen carbonate in water are added at 40° C. and then at this temperature 5.64 g (59.7 mmol) methyl chloroformate is added dropwise over 15 minutes. The mixture is then stirred for an hour at 50° C. and then diluted to about twice the volume with water. The organic phase is separated and the aqueous phase is extracted twice with dichloromethane. The combined organic phases are washed with water, dried with sodium sulphate and filtered. The solvent is carefully distilled from the filtrate under reduced pressure. The oily product usually crystallises within a few hours.

10.5 g (69% of theory) 4-iodo-3-[(1S)-1-methyl-2-methylsulphanylethylimino]-3H-isobenzofuran-1-one are obtained.

HPLC: log P (pH 2.3)=3.87

Preparation of Starting Materials of Structure (III)

Example (IIIa-1)

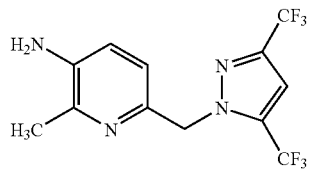

3.1 g (8.75 mmol) 6-{[3,5-bis(trifluoromethyl)-1H-pyrazol-1-yl]methyl}-2-methyl-3-nitropyridine are added to a mixture of 12 g ethanol, 12 g conc. hydrochloric acid and tin(II) chloride dihydrate at 10° C. and the mixture is stirred for 45 minutes at 70° C. The cooled mixture is poured into 50 ml water, made alkaline with 1N sodium hydroxide (pH 10-11) and extracted three times each with methyl-tert.-butylketone and ethyl acetate. The combined organic phases are washed once each time with water and saturated sodium chloride solution, dried over sodium sulphate and filtered. The solvent is carefully distilled from the filtrate under reduced pressure.

2.63 g (84%) 6-{[3,5-bis(trifluoromethyl)-1H-pyrazol-1-yl]methyl}-2-methylpyridin-3-amine are obtained as residue.

HPLC: log P (pH 2.7)=1.90

Example (IIIa-2)

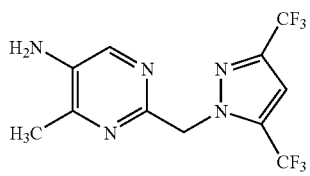

Stage 1

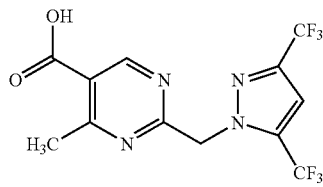

A solution of 6.40 g (16.7 mmol) ethyl 2-(3,5-bistrifluoromethylpyrazol-1-ylmethyl)-4-methylpyrimidine-5-carboxylate (cf. example V-1) in 15 ml ethanol is treated dropwise with a solution of 2.82 g (50.2 mmol) potassium hydroxide in 20 ml ethanol and the reaction mixture is then heated under reflux for 5 hours. After cooling to room temperature the solvent is removed, the residue treated with water and adjusted to pH=1 with conc. hydrochloric acid. The separated crystals are filtered off and dried in vacuo.

6.0 g (92% of theory) 2-(3,5-bistrifluoromethylpyrazol-1-yl-methyl)-4-methylpyrimidin-5-carboxylic acid are obtained.

HPLC: log P (pH 2.3)=2.68

Stage 2

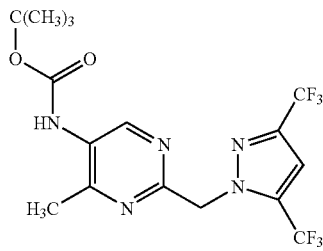

To a solution of 5.00 g (14.1 mmol) 2-(3,5-bistrifluoromethylpyrazol-1-yl-methyl)-4-methylpyrimidine-5-carboxylic acid in 30 ml tert-butanol are added dropwise sequentially 3.89 g (14.1 mmol) diphenylphosphoryl azide and 1.43 g (14.1 mmol) triethylamine. The mixture is heated for 9 hours under reflux, cooled to room temperature and the solvent is removed to a residual volume of ca. 15 ml. The residue is diluted 100 ml dichloromethane and washed sequentially with 0.5 N sodium hydroxide, water, saturated sodium chloride solution and dried over sodium sulphate. Purification of the residue is carried out by chromatography on silica with cyclohexane (2% triethylamine)/ethyl acetate 6:1→3:1 as eluent.

2.60 g (38% of theory) tert-butyl [2-(3,5-bistrifluoromethylpyrazol-1-ylmethyl)-4-methylpyrimidin-5-yl]carbamidate (VI-1) is obtained as pale yellow solid.

HPLC: log P (pH 2.3)=3.84

Stage 3

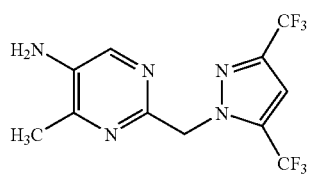

To a solution of 2.50 g (5.88 mmol) tert-butyl [2-(3,5-bistrifluoromethyl-pyrazol-1-ylmethyl)-4-methylpyrimidin-5-yl]carbamidate in 15 ml dichloromethane at 0° C. are added dropwise 8.14 g (71.4 mmol) trifluoroacetic acid. The reaction solution is stirred at this temperature for 30 minutes and then for 3 hours at room temperature. The reaction solution is then added dropwise to an ice-cold, saturated sodium carbonate solution and exhaustively extracted with dichloromethane. After drying the combined organic phases over sodium sulphate and removal of the solvent the product is obtained as a yellow oil.

1.80 g (90% of) 2-(3,5-bis-trifluoromethylpyrazol-1-ylmethyl)-4-methylpyrimidin-5-yl-amine (IIIa-2) are obtained.

HPLC: log P (pH 2.3)=2.43

Example (IIIb-1)

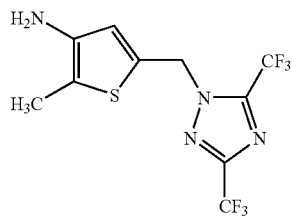

1.0 g (1.5 mmol) 1-[(5-methyl-4-nitro-2-thienyl)methyl]-3,5-bis(trifluoromethyl)-1H-1,2,4-triazole at 10° C. is added to a mixture of 8.0 g ethanol, 8.0 g conc. hydrochloric acid and 2.71 g (12.0 mmol) tin(II) chloride dihydrate and stirred 45 minutes at 70° C. The cooled reaction mixture is poured into 25 ml water, made alkaline with 1N sodium hydroxide (pH 10-11) and extracted several times with methyl-tert.-butylketone and ethyl acetate. The organic phases are washed once each time with water and saturated sodium chloride solution, dried over sodium sulphate and the solvent is then carefully distilled off under reduced pressure.

0.41 g (66% of theory) 5-{[3,5-bis(trifluoromethyl)-1H-1,2,4-triazol-1-yl]methyl}-2-methylthiophene-3-amine are obtained.

HPLC: log P (pH 2.7)=2.2

Preparation of the Starting Materials of Structure (IV)

Example (IV-1)

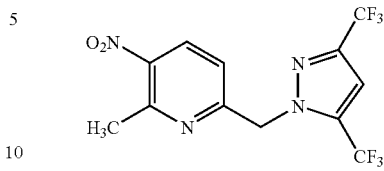

2.9 g (12.55 mmol) 6-(bromomethyl)-2-methyl-3-nitropyridine, 2.65 g (12.55 mmol) 3,5-bis(trifluoromethyl)pyrazole and 4.34 g (31.38 mmol) potassium carbonate in 80 ml N,N-dimethylformamide are stirred under argon for 30 minutes at 60° C. The cooled reaction mixture is filtered, the residue washed with N,N-dimethylformamide and the mother liquor is distilled off. The dark green residue is purified by chromatography on silica with cyclohexane/ethyl acetate 3:1 as eluent.

3.25 g (72% of theory) 6-{[3,5-bis(trifluoromethyl)-1H-pyrazol-1-yl]methyl}-2-methyl-3-nitropyridine are obtained as an orange coloured oil.

HPLC: log P (pH 2.7)=3.8

Preparation of Starting Materials of Structure (V)

Example (V-1)

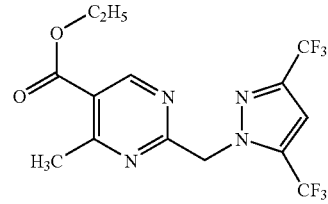

8.69 ml (23.6 mmol) sodium ethylate (21% solution in ethanol) under argon are diluted with 17.5 ml ethanol and treated portionswise with 7.00 g (23.6 mmol) 2-(3,5-bistrifluoromethyl-pyrazol-1-yl)-acetamidine hydrochloride. The reaction mixture is then cooled to 0° C., treated dropwise with 4.40 g (23.6 mmol) ethyl 2-ethoxymethylene-3-oxo-butanoate and the mixture is heated under reflux overnight. After cooling to room temperature the precipitate is filtered off, the filtrate is evaporated and the residue is purified on silica with cyclohexane/ethyl acetate 4:1 as eluent.

3.50 g (38% of theory) ethyl 2-(3,5-bistrifluoromethyl-pyrazol-1-yl-methyl)-4-methylpyrimidine-5-carboxylate is obtained as a yellow oil.

HPLC: log P (pH 2.3)=3.96

Preparation of Starting Materials of Structure (VII)

Example (VII-1)

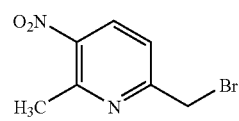

11.6 g (76.2 mmol) 2,6-dimethyl-3-nitropyridine and 1.25 g (7.62 mmol) azodiisobutyronitrile are dissolved in 250 ml tetrachloromethane under argon and heated to 50° C. 14.9 g (83.9 mmol) N-bromosuccinimide are then added and the mixture is stirred 5 hours at reflux under radiation (Hg lamp, 250 W). The solvent is then distilled off under reduced pressure and the residue is purified by chromatography on silica with cyclohexane/ethyl acetate 4:1 as eluent.

5.9 g (26% of theory) 6-(bromomethyl)-2-methyl-3-nitropyridine are obtained as an orange coloured oil.

HPLC: log P (pH 2.7)=2.2

Preparation of Starting Materials of Structure (IX):

Example (IX-1)

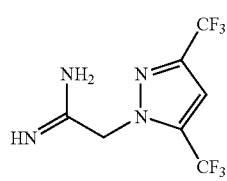

Stage 1

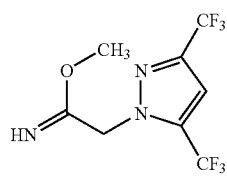

A solution of 100 g (490 mmol) 3,5-bis(trifluoromethyl) pyrazole in 400 ml acetonitrile is treated sequentially with 80.3 g (588 mmol) potassium carbonate and 53.2 g (490 mmol) methyl chloroacetate. The reaction mixture is heated under reflux for 6 hours, cooled to room temperature and the solvent removed. The residue is treated with water and extracted exhaustively with ethyl acetate. The combined organic phases are dried over sodium sulphate and then evaporated.

88 g (59% of theory) methyl (3,5-bistrifluoromethyl-pyrazol-1-yl)acetate is obtained as a yellow oil.

HPLC: log P (pH 2.3)=2.93

Stage 2

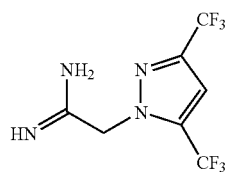

19.4 g (362 mmol) ammonium chloride are suspended in 260 ml toluene under argon, cooled to 0° C. and treated dropwise with 181 ml (362 mmol) aluminium chloride (2 M solution in toluene). The reaction mixture is stirred at room temperature for 1 hour, heated briefly to 60° C. and again cooled to room temperature. After the dropwise addition of 20.0 g (72.4 mmol) methyl (3,5-bistrifluoromethylpyrazol-1-yl)acetate the mixture is stirred overnight at 80° C. The reaction mixture is cooled to 0° C., treated carefully with 150 ml methanol and stirred for 1 hour at room temperature. The salts formed are filtered off and washed with methanol. After evaporation of the filtrate the target compound is obtained as a colourless solid.

13.5 g (60% of theory) 2-(3,5-bistrifluoromethyl-pyrazol-1-yl)acetamidine hydrochloride are obtained.

HPLC: log P (pH 2.3)=0.74

Preparation of Starting Materials of Structure (X)

Example (X-1)

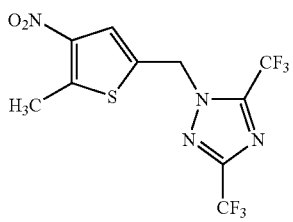

Stage 1

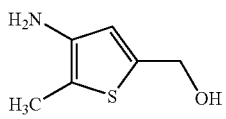

2.9 g (16.94 mmol) 5-methyl-4-nitrothiophene-2-carbaldehyde are dissolved in 60 ml ethanol, 0.32 g (8.47 mmol) sodium borohydride are added at room temperature and reaction mixture is stirred for 20 minutes at 30° C. Half of the solvent is then evaporated, 100 ml water added and extracted with methyl-tert.-butylketone. The organic phase is washed once each time with water and saturated sodium chloride solution, dried over sodium sulphate and evaporated.

2.2 g (64%) (5-methyl-4-nitro-2-thienyl)methanol as an orange-brown oil.

HPLC: log P (pH 2.7)=1.4

Stage 2

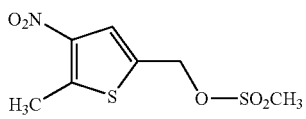

1.0 g (5.77 mmol) (5-methyl-4-nitro-2-thienyl)methanol and 0.76 g (7.51 mmol) triethylamine are dissolved in 10 ml tetrahydrofuran and a solution of 0.66 g (5.77 mmol) methanesulphonyl chloride in 3 ml tetrahydrofuran is slowly added dropwise at <5° C. The solution is stirred for one hour at room temperature. The reaction mixture is carefully evaporated, the residue is taken up in a little ethyl acetate and washed once each time with 1N hydrochloric acid and sodium hydrogen carbonate solution. The organic phase is dried over sodium sulphate, the solvent is distilled off and the residue (5-methyl-4-nitro-2-thienylmethylmethane sulphonate) is used in the next stage without further purification.

Stage 3

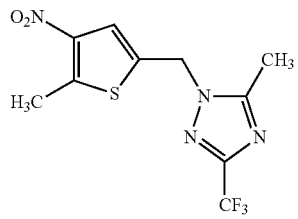

1.0 g (3.98 mmol) (5-methyl-4-nitro-2-thienyl)methyl-methane sulphonate, 0.82 g (3.98 mmol) 3,5-bis(trifluoromethyl)-1H-1,2,4-triazole, 0.93 g (5.97 mmol) potassium carbonate and 0.11 g (0.398 mmol) 18-crown-6 are heated under reflux in acetonitrile for 2 h. The cooled reaction mixture is evaporated, the residue taken up in 20 ml water and extracted three times with ethyl acetate. The combined organic phases are washed with saturated sodium chloride solution, dried over sodium sulphate and the solvent is distilled off under vacuum. The product (1-[(5-methyl-4-nitro-2-thienyl)methyl]-3,5-bis(trifluoromethyl)-1H-1,2,4-triazole) is used in the next stage without purification.

APPLICATION EXAMPLES

Example A

| *Myzus* test (spray test treatment) | |
|---|---|
| Solvent: | 78 parts by weight acetone |
|  | 1.5 parts by weight dimethylformamide |
| Emulsifier: | 0.5 parts by weight alkylarylpolyglycol ether |

For the preparation of a suitable active compound formulation 1 part by weight of the active compound is mixed with the above amounts of solvent and emulsifier and the concentrate is diluted to the desired concentration with water containing emulsifier.

China cabbage slices (*Brassica pekinensis*) that are infected with all stages of the green peach aphid (*Myzus persicae*) are sprayed with an active compound preparation at the desired concentration.

After the desired time the activity in % is determined. Here 100% means that all aphids were killed; 0% means that no aphids were killed.

In this test compounds of preparation examples 1, 2, 5, 6, 7, 8, 9, 13, 14, 15, 16, 18, 19, 20, 21, 22, 23, 24, 28, 29, 30, 31, 34, 36, 37, 38, 39, 40, 41, 64, 65 and 66, for example, demonstrated good activity.

TABLE A

| | Plant-damaging insects Myzus test (spray treatment) | |
|---|---|---|
| Active compound | Active compound concentration in g/ha | Death rate in % after 5$^d$ |
| (6) | 100 | 100 |
| (7) | 100 | 90 |

TABLE A-continued

Plant-damaging insects
Myzus test (spray treatment)

| Active compound | Active compound concentration in g/ha | Death rate in % after 5$^d$ |
|---|---|---|
| (8) | 100 | 100 |
| (1) | 100 | 100 |
| (2) | 100 | 100 |

TABLE A-continued
Plant-damaging insects
Myzus test (spray treatment)
| Active compound | Active compound concentration in g/ha | Death rate in % after 5$^d$ |
|---|---|---|
| 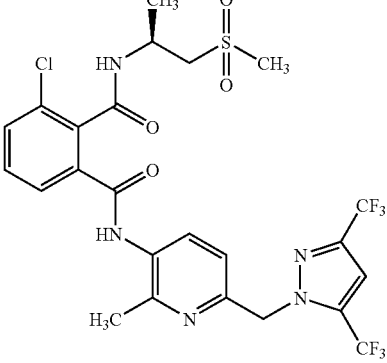 (9) | 100 | 100 |
| 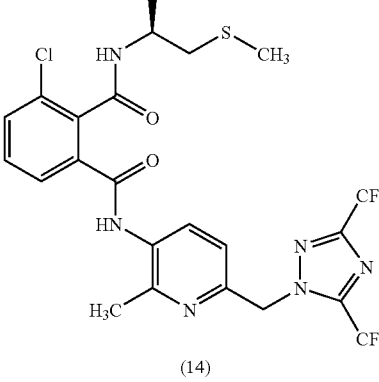 (14) | 100 | 90 |
| 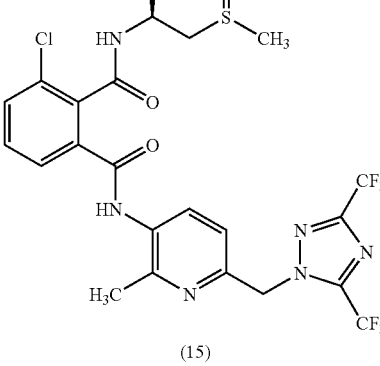 (15) | 100 | 100 |

TABLE A-continued

Plant-damaging insects
Myzus test (spray treatment)

| Active compound | Active compound concentration in g/ha | Death rate in % after 5$^d$ |
|---|---|---|
| (16) | 100 | 100 |
| (13) | 100 | 100 |
| (18) | 100 | 100 |

TABLE A-continued
Plant-damaging insects
Myzus test (spray treatment)
| Active compound | Active compound concentration in g/ha | Death rate in % after 5$^d$ |
|---|---|---|
| 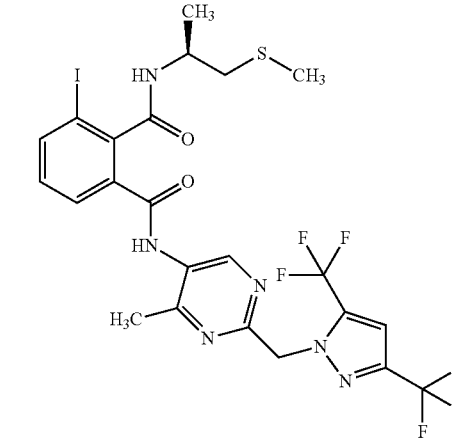 (19) | 100 | 100 |
| 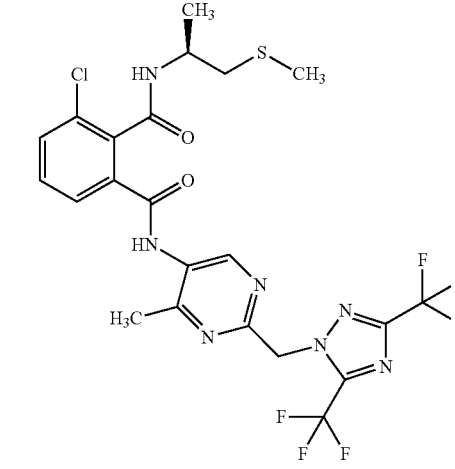 (20) | 100 | 100 |
| 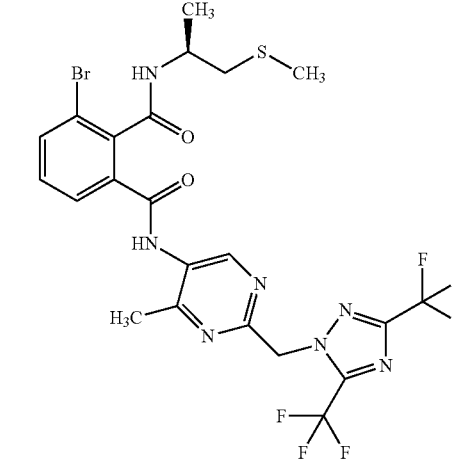 (21) | 100 | 100 |

TABLE A-continued
Plant-damaging insects
Myzus test (spray treatment)
| Active compound | Active compound concentration in g/ha | Death rate in % after 5$^d$ |
|---|---|---|
| 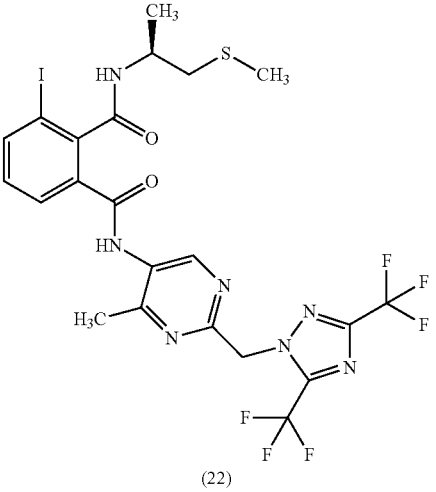 (22) | 100 | 90 |
| 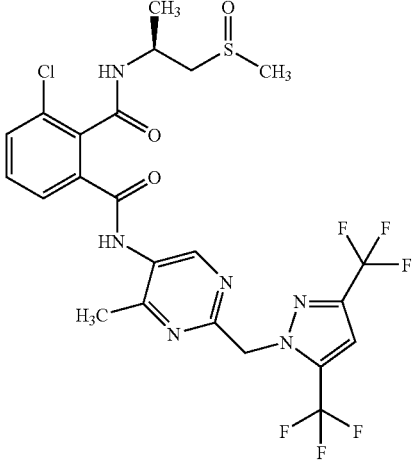 (5) | 100 | 80 |
| 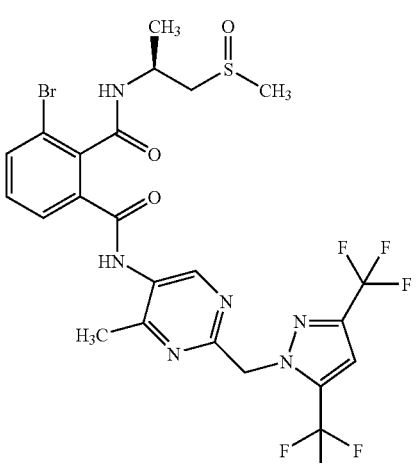 (23) | 100 | 80 |

TABLE A-continued
Plant-damaging insects
Myzus test (spray treatment)
| Active compound | Active compound concentration in g/ha | Death rate in % after 5$^d$ |
|---|---|---|
| 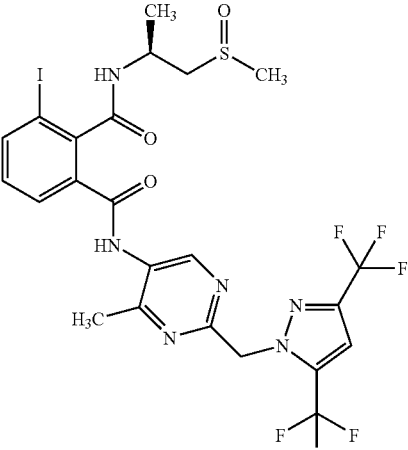<br>(24) | 100 | 100 |
| 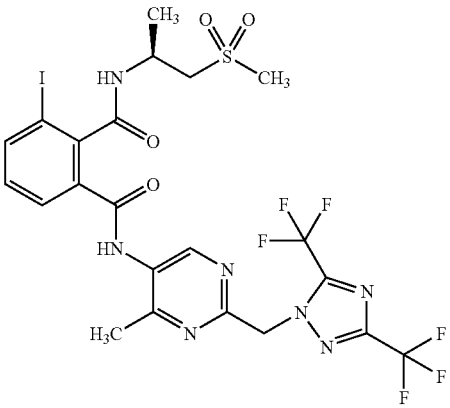<br>(41) | 100 | 90 |
| 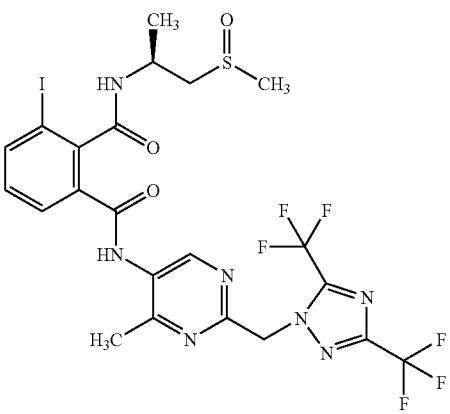<br>(40) | 100 | 100 |

TABLE A-continued

Plant-damaging insects
Myzus test (spray treatment)

| Active compound | Active compound concentration in g/ha | Death rate in % after 5$^d$ |
|---|---|---|
| (39) | 100 | 100 |
| (38) | 100 | 100 |
| (37) | 100 | 100 |

TABLE A-continued
| | Plant-damaging insects Myzus test (spray treatment) | |
|---|---|---|
| Active compound | Active compound concentration in g/ha | Death rate in % after 5$^d$ |
| 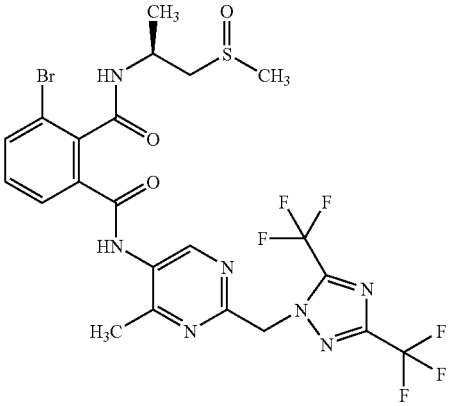<br>(36) | 100 | 100 |
| 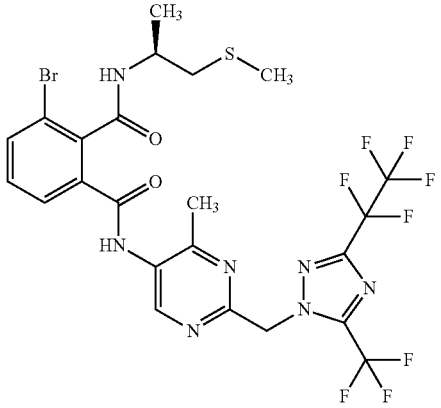<br>(31) | 100 | 100 |
| 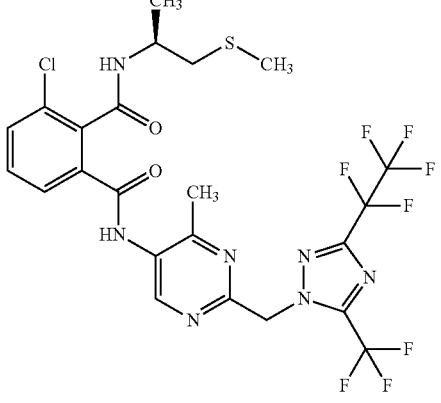<br>(30) | 100 | 90 |

TABLE A-continued

Plant-damaging insects
Myzus test (spray treatment)

| Active compound | Active compound concentration in g/ha | Death rate in % after 5[d] |
|---|---|---|
| (29) | 100 | 100 |
| (28) | 100 | 100 |
| (64) | 100 | 100 |

TABLE A-continued

Plant-damaging insects
Myzus test (spray treatment)

| Active compound | Active compound concentration in g/ha | Death rate in % after 5$^d$ |
|---|---|---|
| 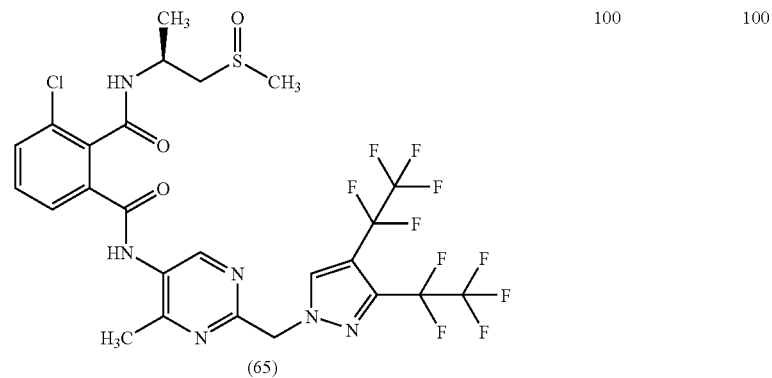 (65) | 100 | 100 |
| 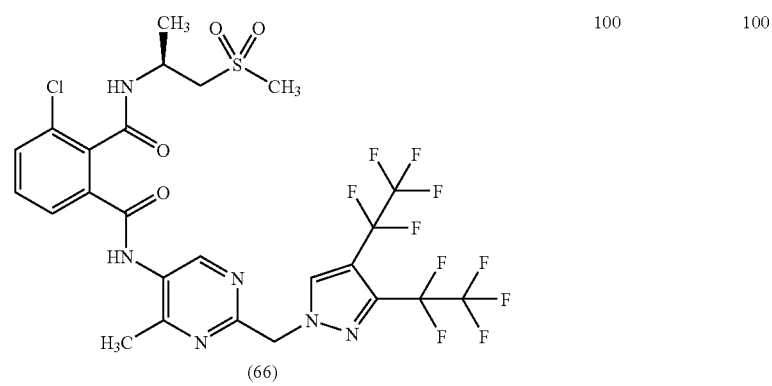 (66) | 100 | 100 |

Example B

| Phaedon test (spray treatment) | |
|---|---|
| Solvent: | 78 parts by weight acetone |
| | 1.5 parts by weight dimethylformamide |
| Emulsifier: | 0.5 parts by weight alkylarylpolyglycol ether |

For the preparation of a suitable active compound formulation 1 part by weight of the active compound is mixed with the above amounts of solvent and emulsifier and the concentrate is diluted to the desired concentration with water containing emulsifier.

China cabbage slices (*Brassica pekinensis*) are sprayed with an active compound preparation of the desired composition and after drying infected with larvae of the mustard leaf beetle (*Phaedon cochleariae*).

After the desired time the activity in % is determined. Here 100% means that all beetle larvae were killed; 0% means that no beetle larvae were killed.

In this test the compounds of the preparation examples 1, 2, 6, 7, 8, 9, 13, 14, 15, 16, 64, 65 and 66, for example, demonstrated good activity.

TABLE B

Plant damaging insects
Phaedon test (spray treatment)

| Active compound | Active compound concentration in g/ha | Death rate in % after 7$^d$ |
|---|---|---|
| (6) | 100 | 100 |
| (7) | 100 | 90 |
| (8) | 100 | 100 |

TABLE B-continued
Plant damaging insects
Phaedon test (spray treatment)
| Active compound | Active compound concentration in g/ha | Death rate in % after 7$^d$ |
|---|---|---|
| (1) 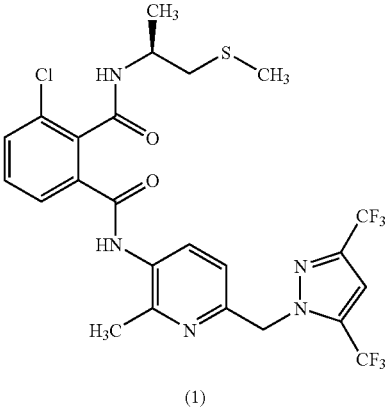 | 100 | 100 |
| (2) 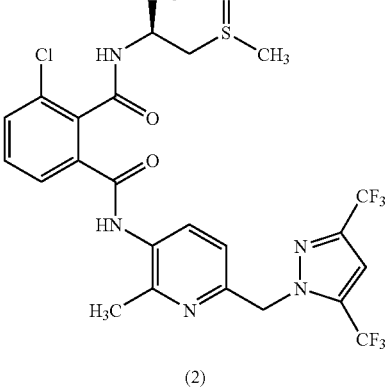 | 100 | 100 |
| (9) 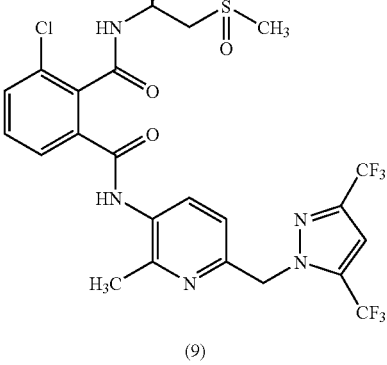 | 100 | 100 |

TABLE B-continued

Plant damaging insects
Phaedon test (spray treatment)

| Active compound | Active compound concentration in g/ha | Death rate in % after 7$^d$ |
|---|---|---|
| (14) | 100 | 90 |
| (15) | 100 | 100 |
| (16) | 100 | 100 |

TABLE B-continued

Plant damaging insects
Phaedon test (spray treatment)

| Active compound | Active compound concentration in g/ha | Death rate in % after 7$^d$ |
|---|---|---|
| (13) | 100 | 100 |
| (64) | 4 | 100 |
| (65) | 4 | 100 |

TABLE B-continued

Plant damaging insects
Phaedon test (spray treatment)

| Active compound | Active compound concentration in g/ha | Death rate in % after $7^d$ |
|---|---|---|
| 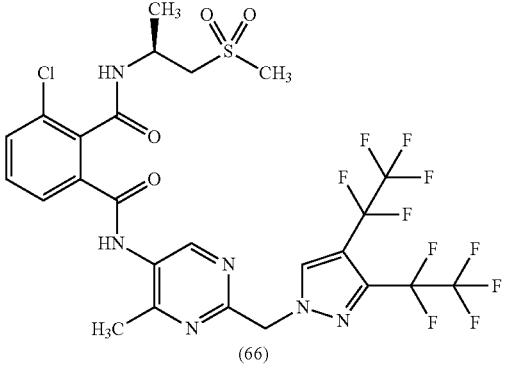 (66) | 4 | 100 |

Example C

| Spodoptera frugiperda test (spray treatment) | |
|---|---|
| Solvent: | 78 parts by weight acetone |
| | 1.5 parts by weight dimethylformamide |
| Emulsifier: | 0.5 parts by weight alkylarylpolyglycol ether |

For the preparation of a suitable active compound formulation 1 part by weight of the active compound is mixed with the above amounts of solvent and emulsifier and the concentrate is diluted to the desired concentration with water containing emulsifier.

Maize leaf sections (*Zea mays*) are sprayed with an active compound preparation of the desired concentration and after drying infected with caterpillars of the fall army worm (*Spodoptera frugiperda*).

After the desired time the activity in % is determined. Here 100% means that all caterpillars were killed; 0% means that no caterpillars were killed.

In this test the compounds of preparation examples 1, 2, 6, 7, 8, 9, 13, 14, 15, 16, 18, 19, 24, 29, 30, 31, 34, 64, 65 and 66, for example, demonstrated good activity.

TABLE C

Plant damaging insects
Spodoptera frugiperda test (spray treatment)

| Active compound | Active compound concentration in g/ha | Death rate in % after $7^d$ |
|---|---|---|
| 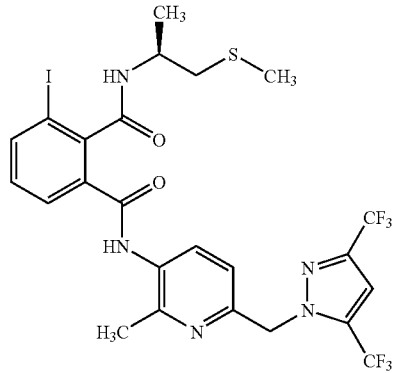 (6) | 4 | 100 |

TABLE C-continued
Plant damaging insects
Spodoptera frugiperda test (spray treatment)
| Active compound | Active compound concentration in g/ha | Death rate in % after 7$^d$ |
|---|---|---|
| 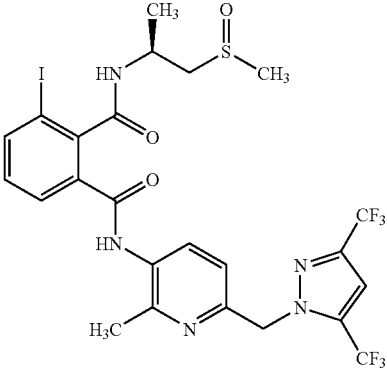<br>(7) | 4 | 100 |
| 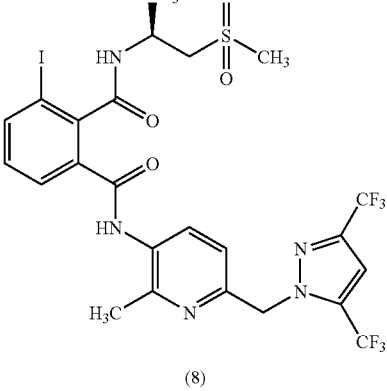<br>(8) | 4 | 100 |
| 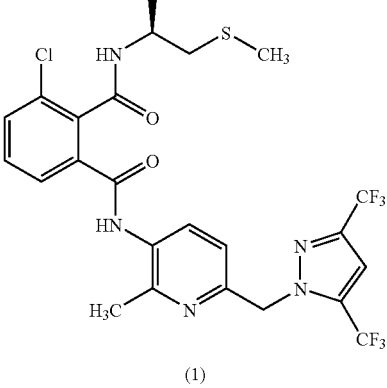<br>(1) | 4 | 100 |

TABLE C-continued
Plant damaging insects
Spodoptera frugiperda test (spray treatment)
| Active compound | Active compound concentration in g/ha | Death rate in % after 7$^d$ |
|---|---|---|
| 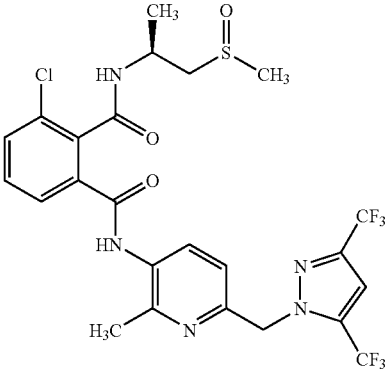<br>(2) | 4 | 100 |
| 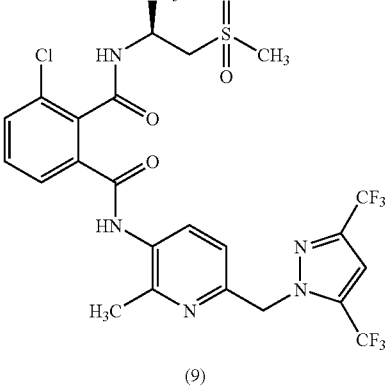<br>(9) | 4 | 100 |
| 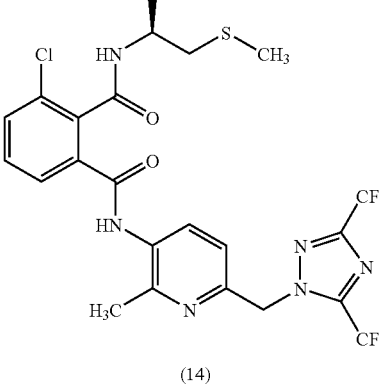<br>(14) | 4 | 100 |

TABLE C-continued
Plant damaging insects
Spodoptera frugiperda test (spray treatment)
| Active compound | Active compound concentration in g/ha | Death rate in % after 7$^d$ |
|---|---|---|
| 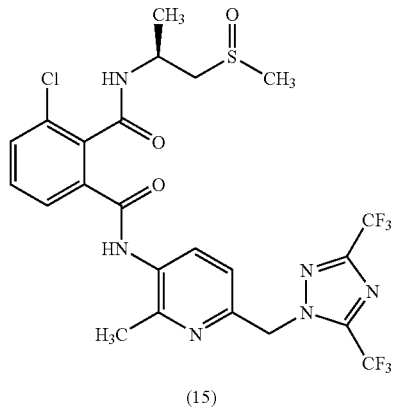<br>(15) | 4 | 100 |
| 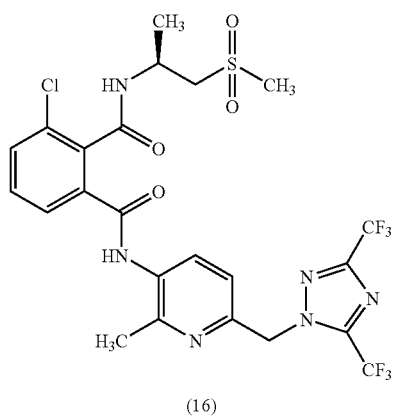<br>(16) | 4 | 100 |
| 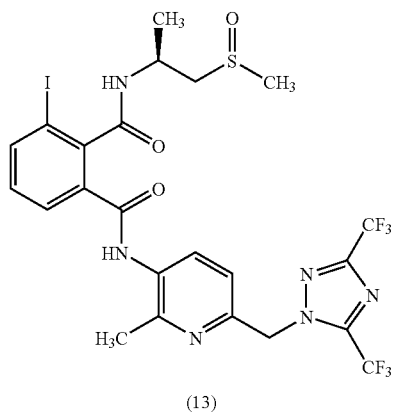<br>(13) | 4 | 100 |

TABLE C-continued
Plant damaging insects
Spodoptera frugiperda test (spray treatment)
| Active compound | Active compound concentration in g/ha | Death rate in % after 7$^d$ |
|---|---|---|
| 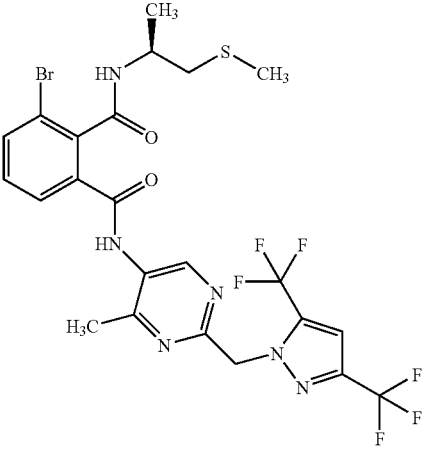 (18) | 4 | 100 |
| 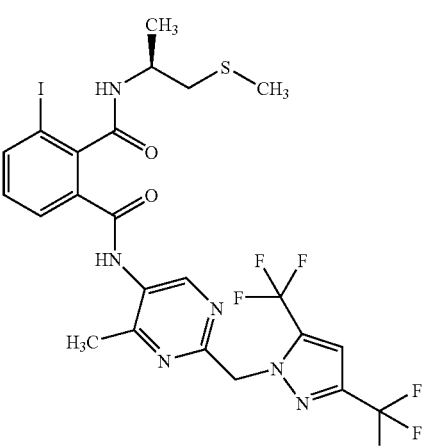 (19) | 4 | 83 |
| 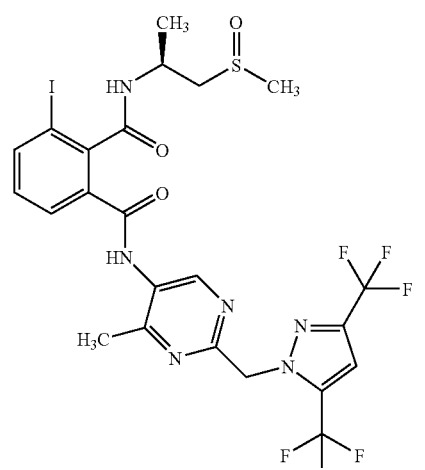 (24) | 4 | 83 |

TABLE C-continued
| | Plant damaging insects | |
|---|---|---|
| | Spodoptera frugiperda test (spray treatment) | |
| Active compound | Active compound concentration in g/ha | Death rate in % after 7$^d$ |
| 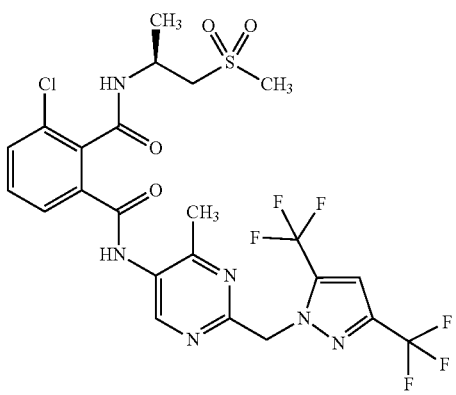 (34) | 4 | 100 |
| 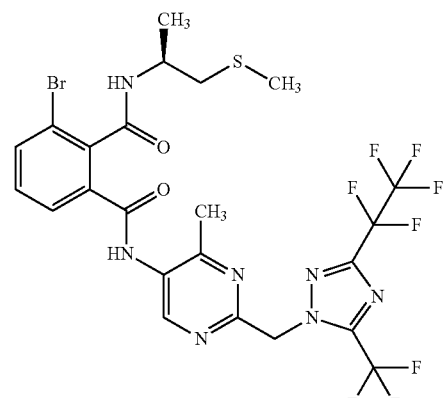 (31) | 4 | 100 |
| 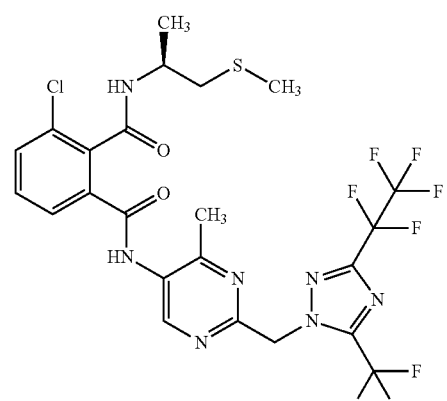 (30) | 4 | 100 |

TABLE C-continued
Plant damaging insects
Spodoptera frugiperda test (spray treatment)
| Active compound | Active compound concentration in g/ha | Death rate in % after 7$^d$ |
|---|---|---|
| 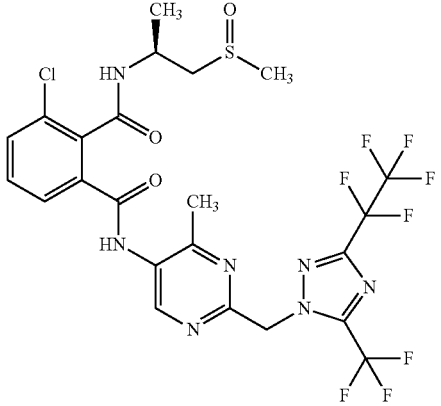 (29) | 4 | 100 |
| 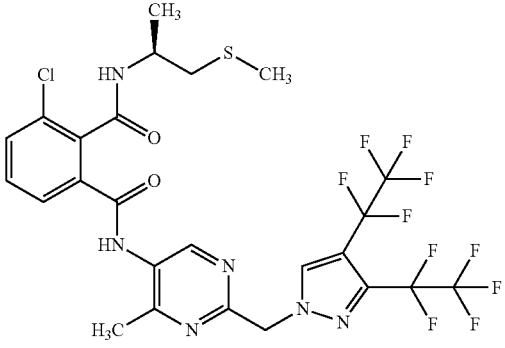 (64) | 4 | 100 |
| 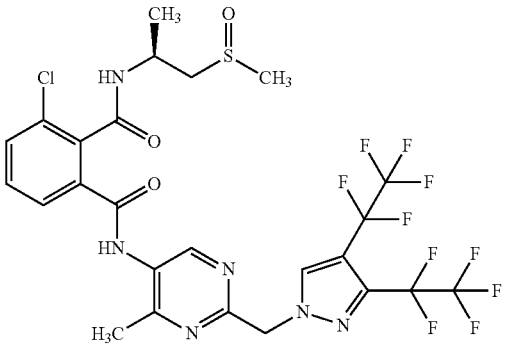 (65) | 4 | 100 |

TABLE C-continued

Plant damaging insects
Spodoptera frugiperda test (spray treatment)

| Active compound | Active compound concentration in g/ha | Death rate in % after $7^d$ |
|---|---|---|
| (66) | 4 | 100 |

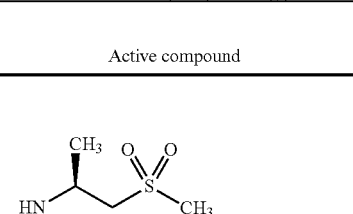

Example D

Plutella test

| | |
|---|---|
| Solvent: | 7 parts by weight dimethylformamide |
| Emulsifier: | 2 parts by weight alkylarylpolyglycol ether |

For the preparation of a suitable active compound formulation 1 part by weight of the active compound is mixed with the above amounts of solvent and emulsifier and the concentrate is diluted to the desired concentration with water containing emulsifier.

Cabbage leaves (*Brassica oleracea*) are treated by dipping into the active compound preparation of the desired concentration and infected with caterpillars of the diamond back moth (*Plutella xylostella*) while the leaves were still wet.

After the desired time the death rate is determined as %. Here 100% means that all caterpillars were killed; 0% means no caterpillars were killed.

In this test the compounds of the preparation examples 6, 13, 16 and 66, for example, demonstrated good activity.

TABLE D

Plant damaging insects
Plutella Test

| Active compound | Active compound concentration in ppm | Death rate in % after $7^d$ |
|---|---|---|
| (6) | 0.8 | 100 |

TABLE D-continued

Plant damaging insects
Plutella Test

| Active compound | Active compound concentration in ppm | Death rate in % after 7$^d$ |
|---|---|---|
| (16) | 0.16 | 100 |
| (13) | 0.16 | 95 |
| (66) | 0.8 | 100 |

Example E

*Aphis gossypii* test

| | |
|---|---|
| Solvent: | 7 parts by weight dimethylformamide |
| Emulsifier: | 2 parts by weight alkylarylpolyglycol ether |

For the preparation of a suitable active compound formulation 1 part by weight of the active compound is mixed with the above amounts of solvent and emulsifier and the concentrate is diluted to the desired concentration with water containing emulsifier.

Cotton leaves (*Gossypium hirsutum*) heavily infested with the cotton aphid (*Aphis gossypii*) are treated by immersion in the active compound preparation at the desired concentration.

After the desired time the death rate in % is determined. Here 100% means that all aphids were killed; 0% means that no aphids were killed.

In this test compounds of preparation examples 6, 16 and 65, for example, demonstrated good activity.

TABLE E

Plant damaging insects
Aphis gossypii Test

| Active compound | Active compound concentration in ppm | Death rate in % after 7$^d$ |
|---|---|---|
| 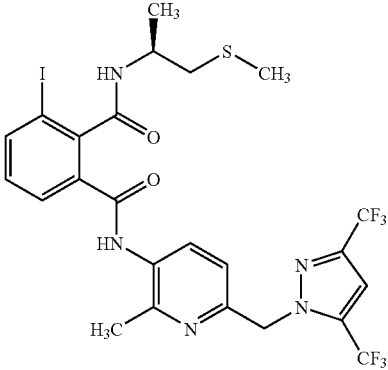 (6) | 20 | 95 |
| 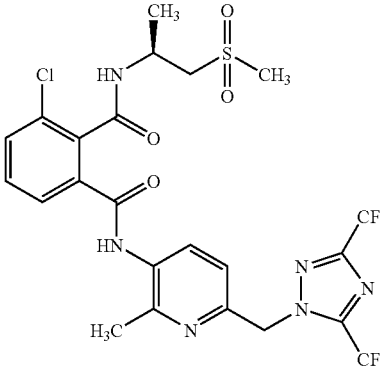 (16) | 100 | 80 |
| 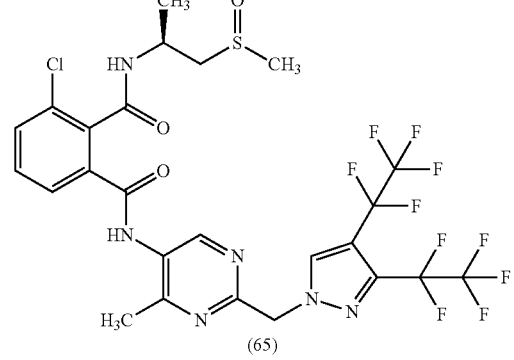 (65) | 100 | 80 |

Example F

*Spodoptera exigua* test (resistant strain)

| Solvent: | 7 parts by weight dimethylformamide |
|---|---|
| Emulsifier: | 2 parts by weight alkylarylpolyglycol ether |

For the preparation of a suitable active compound formulation 1 part by weight of the active compound is mixed with the above amounts of solvent and emulsifier and the concentrate is diluted to the desired concentration with water containing emulsifier.

Cabbage leaves (*Brassica oleracea*) are treated by dipping in the active compound preparation at the desired concentration and infected with caterpillars of the beet army worm (*Spodoptera exigua*) while the leaves are still moist.

After the desired time the death rate in % is determined. Here 100% means that all caterpillars were killed; 0% means that no caterpillars were killed.

In this test compounds of preparation examples 9 and 66, for example, demonstrated good activity.

TABLE F

Plant damaging insects
Spodoptera exigua Test (resistant strain)

| Active compound | Active compound in ppm | Death rate in % after 7$^d$ |
|---|---|---|
| 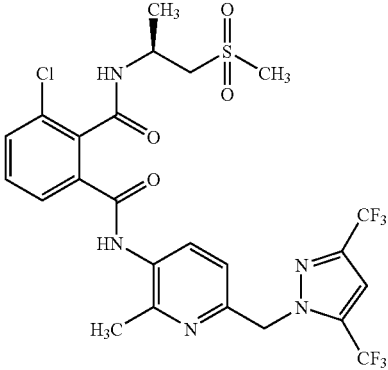 (9) | 0.8 | 80 |
| 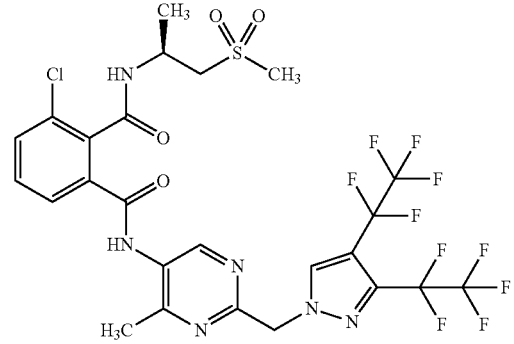 (66) | 4 | 100 |

Example G

| *Tetranychus* Test OP resistant | |
|---|---|
| Solvent: | 78 parts by weight acetone |
| | 1.5 parts by weight dimethylformamide |
| Emulsifier: | 0.5 parts by weight alkylarylpolyglycol ether |

For the preparation of a suitable active compound formulation 1 part by weight of the active compound is mixed with the above amounts of solvent and emulsifier and the concentrate is diluted to the desired concentration with water containing emulsifier.

Bean leaf slices (*Phaseolus vulgaris*) that are infested by all stages of the two-spotted spider mite (*Tetranychus urticae*) are sprayed with an active substance preparation at the desired concentration.

After the desired time the action in % is determined. Here 100% means that all spider mites were killed; 0% means that no spider mites were killed.

In this test compound 64 of the preparation examples, for example, demonstrated good activity.

TABLE G

Plant damaging insects
Tetranychus Test OP resistant

| Active compound | Active compound concentration in g/ha | Death rate in % after 5$^d$ |
|---|---|---|
| 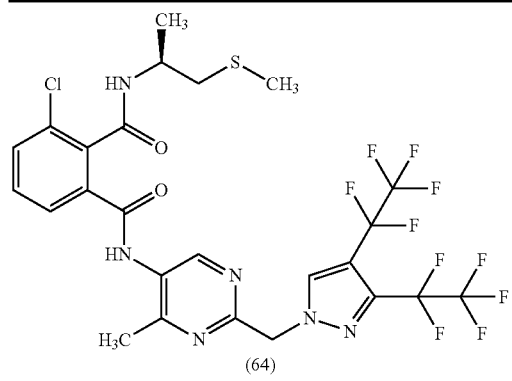<br>(64) | 100 | 100 |

Example H

| Myzus persicae test; hydroponic treatment | |
|---|---|
| Solvent: | 7 parts by weight dimethylformamide |
| Emulsifier: | 2 parts by weight alkylarylpolyglycol ether |

For the preparation of a suitable active compound formulation 1 part by weight of the active compound is mixed with the above amounts of solvent and emulsifier and the concentrate is diluted to the desired concentration with water.

The active compound preparation is mixed with water. The concentration given refers to the amount of active compound per unit volume of water (mg/l=ppm). The treated water is placed in a vessel with a pea plant (*Pisum sativum*) which is then infection with the green peach aphid (*Myzus persicae*) is carried out.

After the desired time the death rate in % is determined. Here 100% means that all aphids were killed, 0% means that no aphids were killed.

In this test the following compounds of the preparation example, for example, demonstrated good activity: 24 and 41

TABLE H

Plant damaging insects
Myzus persicae test; hydroponic treatment

| Active compound | Active compound concentration in ppm | Death rate in % after 6$^d$ |
|---|---|---|
| 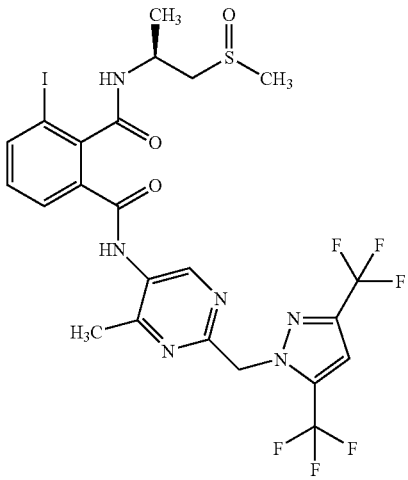<br>(24) | 20 | 95 |

TABLE H-continued

Plant damaging insects
Myzus persicae test; hydroponic treatment

| Active compound | Active compound concentration in ppm | Death rate in % after 6$^d$ |
|---|---|---|
| 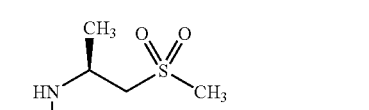 (41) | 20 | 95 |

Example I

| Heliothis armigera test | |
|---|---|
| Solvent: | 7 parts by weight dimethylformamide |
| Emulsifier: | 2 parts by weight alkylarylpolyglycol ether |

For the preparation of a suitable active compound formulation 1 part by weight of the active compound is mixed with the above amounts of solvent and emulsifier and the concentrate is diluted to the desired concentration with water containing emulsifier.

Soy bean leaves (*Glycine max.*) are treated by dipping into the active compound preparation at the desired concentration and infected with the caterpillars of the cotton boll worm (*Heliothis armigera*), while the leaves are still wet.

After the desired time the death rate in % is determined. Here 100% means that all caterpillars were killed; 0% means that no caterpillars were killed.

In this test compound 66 of the preparation examples, for example, demonstrated good activity.

TABLE I

Plant damaging insects
Heliothis armigera Test

| Active compound | Active compound concentration in ppm | Death rate in % after 7$^d$ |
|---|---|---|
| 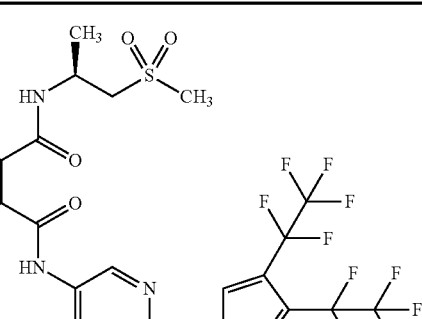 (66) | 0.8 | 80 |

The invention claimed is:
1. A compound of formula (I)

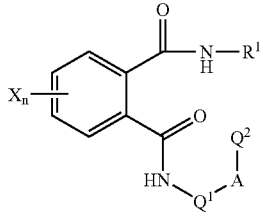

in which
n is 0, 1, 2, 3 or 4,
A is O, S, SO, $SO_2$, NH, $N(C_1-C_4$-alkyl), or a straight-chain or branched alkanediyl with 1 to 10 carbon atoms, optionally substituted by cyano, halo or $C_1-C_6$-alkoxy and optionally interrupted by O, S, SO, $SO_2$, NH or $N(C_1-C_4$-alkyl),
$Q^1$ and $Q^2$ are independently a heterocycle with up to 10 carbon atoms and at least one heteroatom selected from the group consisting of O, S, and N, optionally substituted by nitro, cyano, halo or $A^2-X^2$, wherein $A^2$ is O, S, SO, $SO_2$, $OSO_2$, $NHSO_2$, CO, OCO, NHCO, or a straight-chain or branched alkanediyl with 1 to 10 carbon atoms, and $X^2$ is alkyl with 1 to 10 carbon atoms optionally substituted by hydroxy, cyano, halo, $C_1-C_6$-alkoxy, $C_1-C_6$-alkylthio, $C_1-C_6$-alkylsulpinyl, $C_1-C_6$-alkylsulphonyl, $C_1-C_6$-alkylcarbonyl, $C_1-C_6$-alkoxyimino, $C_1-C_6$-alkoxycarbonyl, or alkenyl or $C_2-C_{10}$-alkynyl optionally substituted by cyano, halo, $C_1-C_6$-alkoxycarbonyl, or cycloalkyl with 3 to 6 carbon atoms optionally substituted by cyano, halo, $C_1-C_6$-alkyl, or $C_6-C_{10}$-aryl optionally substituted by nitro, cyano, carboxy, carbamoyl, thiocarbamoyl, halo, $C_1-C_6$-alkyl, $C_1-C_6$-haloalkyl, $C_1-C_6$-alkoxy, $C_1-C_6$-haloalkoxy, $C_1-C_6$-alkylthio, $C_1-C_6$-haloalkylthio, $C_1-C_6$-alkylsulphinyl, $C_1-C_6$-haloalkylsulphinyl, $C_1-C_6$-alkylsulphonyl, $C_1-C_6$-haloalkylsulphonyl, di($C_1-C_6$-alkyl)aminosulphonyl, $C_1-C_6$-alkylcarbonyl, $C_1-C_6$-alkoxyimino-$C_1-C_6$-alkyl, $C_1-C_6$-alkoxycarbonyl, $C_1-C_6$-alkylaminocarbonyl or di($C_1-C_6$-alkyl)aminocarbonyl,
$R^1$ is hydrogen or $A^1-X^1$, wherein $A^1$ is O, S, SO, $SO_2$, NH, CO, COO, or a straight-chain or branched alkanediyl with 1 to 10 carbon atoms, and $X^1$ is alkyl with 1 to 10 carbon atoms optionally substituted by hydroxy, cyano, carbamoyl, hydroxyimino, halo, $C_1-C_6$-alkoxy, $C_1-C_6$-alkylthio, $C_1-C_6$-alkylsulphinyl, $C_1-C_6$-alkylsulphonyl, $C_1-C_6$-alkylaminosulphonyl, $C_1-C_6$-alkylcarbonyl, $C_1-C_6$-alkylcarbonylamino, $C_1-C_6$-alkylaminocarbonyloxy, di($C_1-C_6$-alkyl)aminocarbonyloxy, $C_1-C_6$-alkoxyimino, $C_1-C_6$-alkoxycarbonyl $C_1-C_6$-alkoxycarbonyl, $C_1-C_6$-alkylaminocarbonyl or di($C_1-C_6$-alkyl)aminocarbonyl, or $C_2-C_{10}$-alkenyl or $C_2-C_{10}$-alkynyl in each case optionally substituted by cyano, halo or $C_1-C_6$-alkoxycarbonyl, or $C_3-C_6$-cycloalkyl or $C_3-C_6$-cycloalkenyl in each case optionally substituted by cyano, halo, $C_1-C_6$-alkyl, $C_1-C_6$-alkoxy or $C_1-C_6$-alkoxycarbonyl, or $C_6-C_{10}$-aryl optionally substituted by nitro, cyano, carboxy, carbamoyl, thio-carbamoyl, halo, $C_1-C_6$-alkyl, $C_1-C_6$-haloalkyl, $C_1-C_6$-alkoxy, $C_1-C_6$-haloalkoxy, $C_1-C_6$-alkylthio, $C_1-C_6$-haloalkylthio, $C_1-C_6$-alkylsulphinyl, $C_1-C_6$-haloalkylsulphinyl, $C_1-C_6$-alkylsulphonyl, $C_1-C_6$-haloalkylsulphonyl, di($C_1-C_6$-alkyl)aminosulphonyl, $C_1-C_6$-alkylcarbonyl, $C_1-C_6$-alkoxyimino-$C_1-C_6$-alkyl, $C_1-C_6$-alkoxycarbonyl, $C_1-C_6$-alkylaminocarbonyl or di($C_1-C_6$-alkyl)aminocarbonyl, or heterocyclyl with up to 10 carbon atoms, up to 5 nitrogen atoms and/or an oxygen atom, sulfur atom or nitrogen atom, and/or SO or $SO_2$ optionally substituted by nitro, cyano, carboxy, carbamoyl, thiocarbamoyl, halo, $C_1-C_6$-alkyl, $C_1-C_6$-haloalkyl, $C_1-C_6$-alkoxy, $C_1-C_6$-haloalkoxy, $C_1-C_6$-alkylthio, $C_1-C_6$-haloalkylthio, $C_1-C_6$-alkylsulphinyl, $C_1-C_6$-haloalkylsulphinyl, $C_1-C_6$-alkylsulphonyl, $C_1-C_6$-haloalkylsulphonyl, di($C_1-C_6$-alkyl)aminosulphonyl, $C_1-C_6$-alkylcarbonyl, $C_1-C_6$-alkoxycarbonyl, $C_1-C_6$-alkylaminocarbonyl and/or di($C_1-C_6$-alkyl)aminocarbonyl,
X is nitro, cyano, halo or $A^2-X^2$, wherein $A^2$ is O, S, SO, $SO_2$, $OSO_2$, $NHSO_2$, CO, OCO, NHCO, or a straight-chain or branched alkanediyl with 1 to 10 carbon atoms, and $X^2$ is $C_1-C_{10}$-alkyl optionally substituted by hydroxy, cyano, halo, $C_1-C_6$-alkoxy, $C_1-C_6$-alkylthio, $C_1-C_6$-alkylsulphinyl, $C_1-C_6$-alkylsulphonyl, $C_1-C_6$-alkylcarbonyl, $C_1-C_6$-alkoxyimino or $C_1-C_6$-alkoxycarbonyl, or $C_2-C_{10}$-alkenyl or $C_2-C_{10}$-alkynyl in each case optionally substituted by cyano, halo and/or $C_1-C_6$-alkoxycarbonyl, or $C_3-C_6$-cycloalkyl optionally substituted by cyano, halo and/or $C_1-C_6$-alkyl, or $C_6-C_{10}$-aryl optionally substituted by nitro, cyano, carboxy, carbamoyl, thiocarbamoyl, halo, $C_1-C_6$-alkyl, $C_1-C_6$-haloalkyl, $C_1-C_6$-alkoxy, $C_1-C_6$-haloalkoxy, $C_1-C_6$-alkylthio, $C_1-C_6$-haloalkylthio, $C_1-C_6$-alkylsulphinyl, $C_1-C_6$-haloalkylsulphinyl, $C_1-C_6$-alkylsulphonyl, $C_1-C_6$-haloalkylsulphonyl, di($C_1-C_6$-alkyl)aminosulphonyl, $C_1-C_6$-alkylcarbonyl, $C_1-C_6$-alkoxyimino-$C_1-C_6$-alkyl, $C_1-C_6$-alkoxycarbonyl, $C_1-C_6$-alkylaminocarbonyl and/or di($C_1-C_6$-alkyl)aminocarbonyl.

2. A compound of formula (IA)

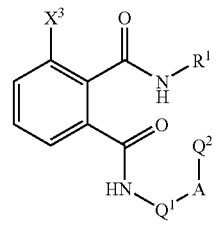

in which
A is methylene,
$Q^1$ is

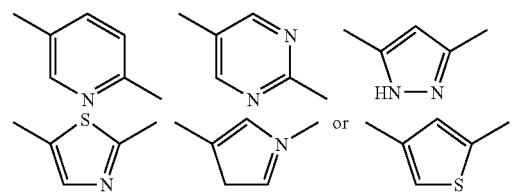

in each case optionally substituted by one or two of nitro, cyano, fluoro, chloro, bromo, iodo, methyl, ethyl, trifluoromethyl, methoxy, ethoxy, methylthio, ethylthio, methylsulphinyl, ethylsulphinyl, methylsulphonyl, or ethylsulphonyl, Q² is

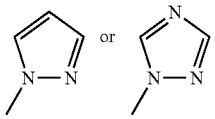 or in each case optionally substituted by cyano, fluoro, chloro, bromo, iodo, methyl, ethyl, n-propyl, isopropyl, n-butyl, isobutyl, sec-butyl, tert-butyl, fluoromethyl, difluoromethyl, trifluoromethyl, chlorodifluoromethyl, fluoroethyl, chloroethyl, difluoroethyl, dichloroethyl, chlorofluoroethyl, trifluoroethyl, trichloroethyl, chlorodifluoroethyl, fluorodichloroethyl, tetrafluoroethyl, pentafluoroethyl, hexafluoropropyl, heptafluoropropyl, methoxy, ethoxy, methylthio, ethylthio, methylsulphinyl, ethylsulphinyl, methylsulphonyl, or ethylsulphonyl, $R^1$ is methyl, ethyl, propyl, butyl, cyano, carbamoyl, hydroximino, fluoro, chloro, bromo, iodo, methoxy, ethoxy, propoxy, butoxy, methylthio, ethylthio, propylthio, butylthio, methylsulphinyl, ethylsulphinyl, propylsulphinyl, methylsulphonyl, ethylsulphonyl, methylaminosulphonyl, ethylaminosulphonyl, propylaminosulphonyl, butylminosulphonyl, acetyl, propionyl, n-butyroyl, isobutyroyl, acetylamino, propionylamino, n-butyroylamino, isobutyroylamino, methylaminocarbonyloxy, ethylaminocarbonyloxy, propylaminocarbonyloxy, dimethylaminocarbonyloxy, diethylaminocarbonyloxy, methoximino, ethoximino, propoximino, butoximino, methoxycarbonyl, ethoxycarbonyl, propxycarbonyl, butoxycarbonyl, methylaminocarbonyl, ethylaminocarbonyl, propylaminocarbonyl, dimethylaminocarbonyl or diethylaminocarbonyl, and $X^3$ is chloro, bromo, iodo, methylsulphonyloxy or ethylsulphonyloxy.

3. A compound according to claim 1, wherein X is chloro, bromo or iodo.

4. A method for the preparation of a compound according to claim 1 comprising, reacting a compound of formula (II)

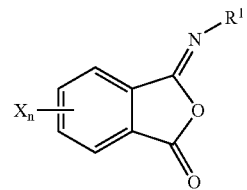

(II)

in which, n, $R^1$ and X have the same meanings as defined in claim 1, with a compound of formula (III)

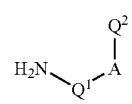

(III)

in which,

A, $Q^1$ and $Q^2$ have the same meanings as defined in claim 1, optionally in the presence of a reaction auxiliary and optionally in the presence of a diluent.

5. A compound according to claim 1, wherein A is methylene.

6. A method for controlling pests comprising contacting pests and/or their habitat with at least one compound according to claim 1.

7. A compound according to claim 1, wherein n is 1 or 2.

8. A method according to claim 4, wherein n is 1 or 2.

9. A method for controlling pests comprising contacting pests and/or their habitat with at least one compound according to claim 2.

10. A method for controlling pests comprising contacting pests and/or their habitat with at least one compound according to claim 3.

11. A method for controlling pests comprising contacting pests and/or their habitat with at least one compound according to claim 5.

12. A method for controlling pests comprising contacting pests and/or their habitat with at least one compound according to claim 7.

* * * * *